United States Patent
Ahlin et al.

(10) Patent No.: US 6,604,019 B2
(45) Date of Patent: Aug. 5, 2003

(54) AUTOMATED PHARMACEUTICAL MANAGEMENT AND DISPENSING SYSTEM

(75) Inventors: Arnold C. Ahlin, deceased, late of Seattle, WA (US), by Marilynn Ahlin, legal representative; John R. Wilson, Bothell, WA (US); Ronald H. Wilson, Bothell, WA (US); Michael F. Smith, Seattle, WA (US)

(73) Assignee: NextRx Corporation, Bothell, WA (US)

( * ) Notice: Subject to any disclaimer, the term of this patent is extended or adjusted under 35 U.S.C. 154(b) by 0 days.

(21) Appl. No.: 09/753,315

(22) Filed: Dec. 29, 2000

(65) Prior Publication Data

US 2002/0095238 A1 Jul. 18, 2002

Related U.S. Application Data

(62) Division of application No. 09/085,968, filed on May 27, 1998, now Pat. No. 6,219,587.

(51) Int. Cl.[7] .............................................. G06F 17/00
(52) U.S. Cl. ........................ 700/231; 700/243; 221/2; 221/3
(58) Field of Search ................... 700/231, 232, 700/243, 237, 235, 242, 236; 221/2–3

(56) References Cited

U.S. PATENT DOCUMENTS

| | | | | |
|---|---|---|---|---|
| 4,811,764 A | * | 3/1989 | McLaughlin ................. 141/98 |
| 4,857,716 A | * | 8/1989 | Gombrich et al. ........... 235/462 |
| 4,967,928 A | * | 11/1990 | Carter ........................... 221/2 |
| 5,014,875 A | * | 5/1991 | McLaughlin et al. ........... 221/2 |
| 5,259,668 A | * | 11/1993 | Teufel et al. ............ 312/249.11 |
| 5,502,944 A | * | 4/1996 | Kraft et al. ..................... 53/55 |
| 5,536,084 A | * | 7/1996 | Curtis et al. ................ 369/75.1 |
| 5,564,593 A | * | 10/1996 | East, Sr. ......................... 221/3 |
| 5,673,983 A | * | 10/1997 | Carlson et al. ............. 312/218 |
| 5,797,515 A | * | 8/1998 | Liff et al. ...................... 221/2 |
| 5,805,051 A | * | 9/1998 | Herrmann et al. ........ 340/309.4 |
| 5,805,456 A | * | 9/1998 | Higham et al. .............. 700/236 |
| 5,905,653 A | * | 5/1999 | Higham et al. .............. 700/244 |
| 6,151,536 A | * | 11/2000 | Arnold et al. ............... 700/237 |
| 6,163,737 A | * | 12/2000 | Fedor et al. ................. 700/236 |
| 6,170,929 B1 | * | 1/2001 | Wilson et al. ............... 312/268 |
| 6,175,779 B1 | * | 1/2001 | Barrett ........................ 700/242 |
| 6,189,727 B1 | * | 2/2001 | Shoenfeld ..................... 221/2 |
| 6,219,587 B1 | * | 4/2001 | Ahlin et al. ................. 700/233 |

\* cited by examiner

*Primary Examiner*—John Follansbee
*Assistant Examiner*—Ronald D Hartman, Jr.
(74) *Attorney, Agent, or Firm*—Jensen & Puntigam, P.S.

(57) ABSTRACT

The system for automatically dispensing medications or other medical elements includes several groupings, i.e. vaults, of storage members, each vault containing approximately 100 individual cartridges, which each contain packages of unit-of-use doses of a given medication or other medical supply, such as syringes. Each storage member includes an ejector which ejects selected medications/supplies to a supply trough. The packages in the trough are moved to a central collator, which dispenses them to a bin receptacle which has been moved underneath the collator and which is typically identified with a particular patient. Information concerning medications/supplies for a particular patient is stored in a system database and used to determine the particular medications/supplies dispensed into a given bin. Bar coding is used to maintain control over the bins, and the medications, forming a closed information/control system. Particular medications and/or supplies which are not available in the automatic dispensing system are supplied from a supplemental medications cart which has been previously stocked with the correct additional medications by virtue of information from a control computer. The filled bins are transferred to a medication cart which can only be accessed as a result of a command signal after a particular patient and his/her associated bin have been matched. A nurse, having access to the correct bin and sector thereof, removes the medications from the cart and administers them to the patient.

2 Claims, 17 Drawing Sheets

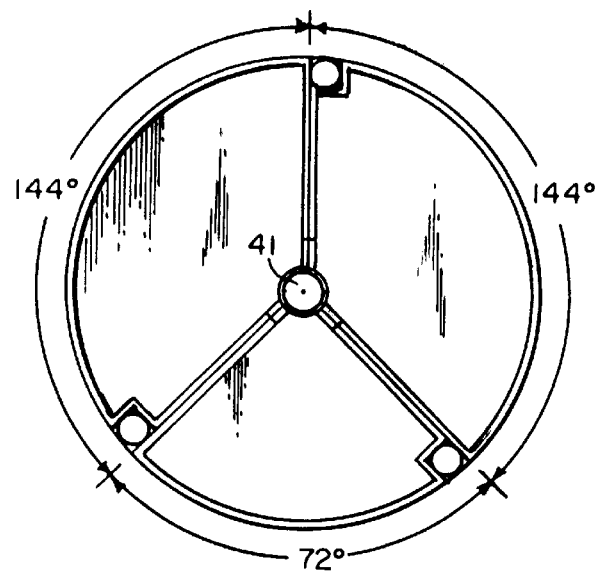
FIG. 4
FIG. 5
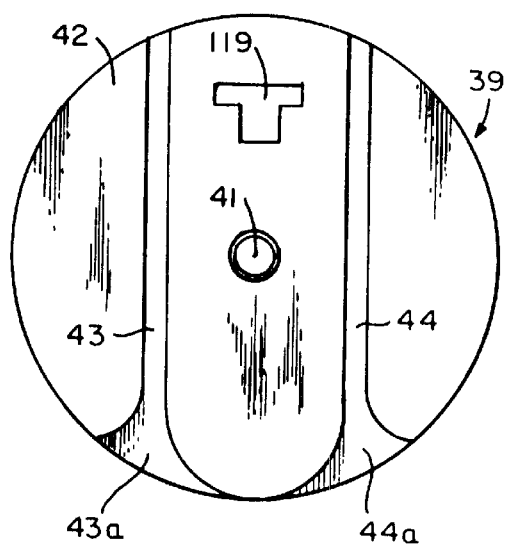
FIG. 6
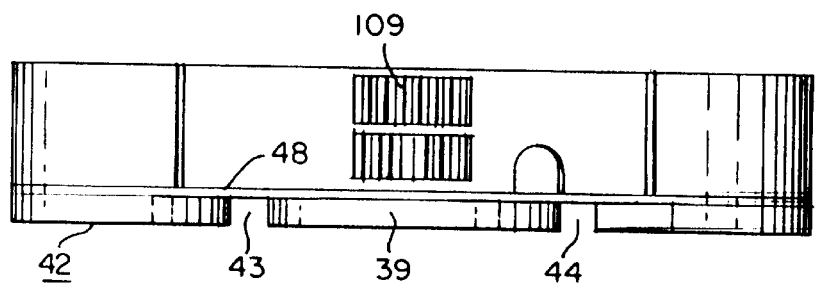

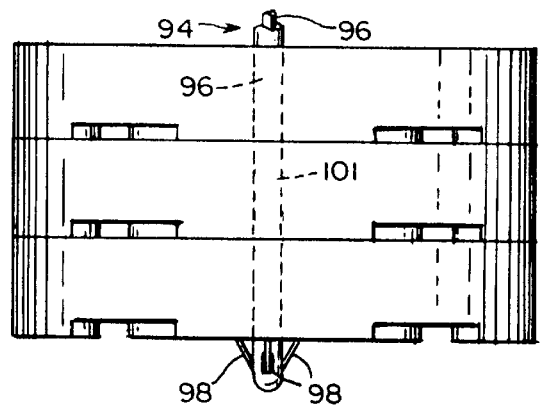
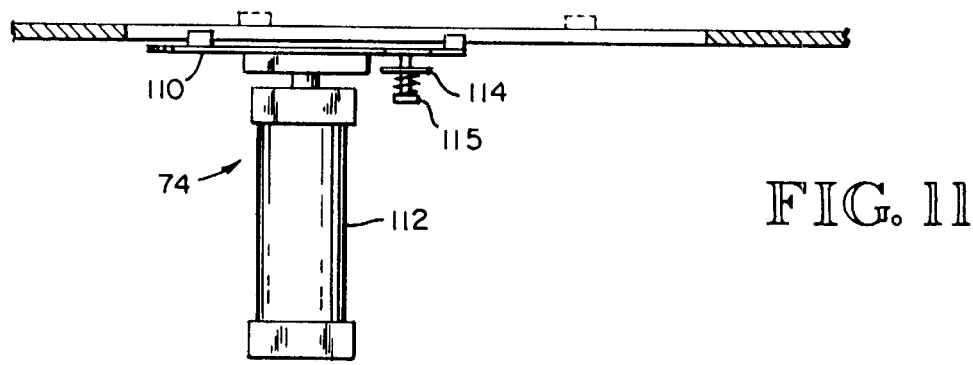
FIG. 11
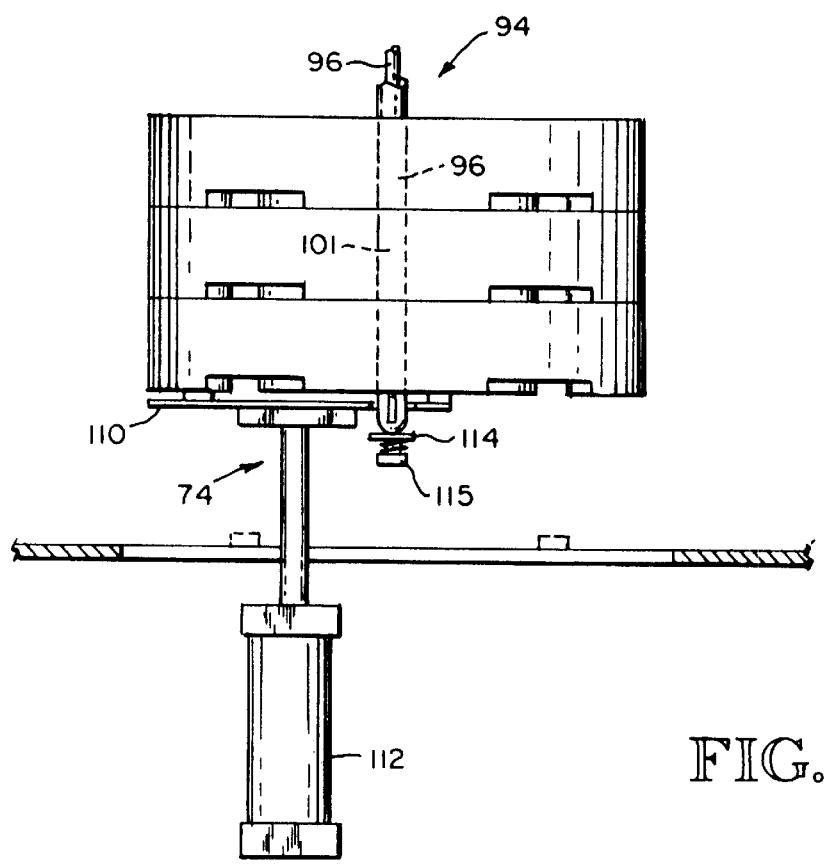
FIG. 12

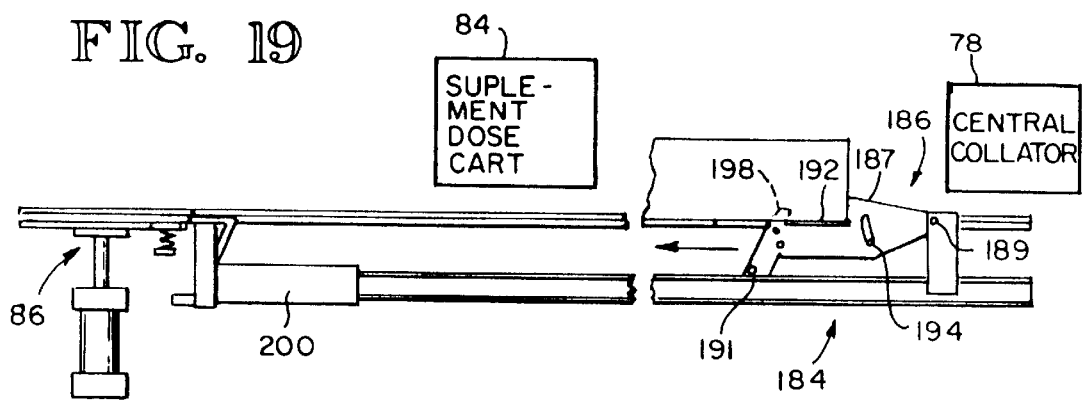
FIG. 19
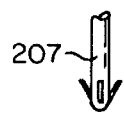
FIG. 20
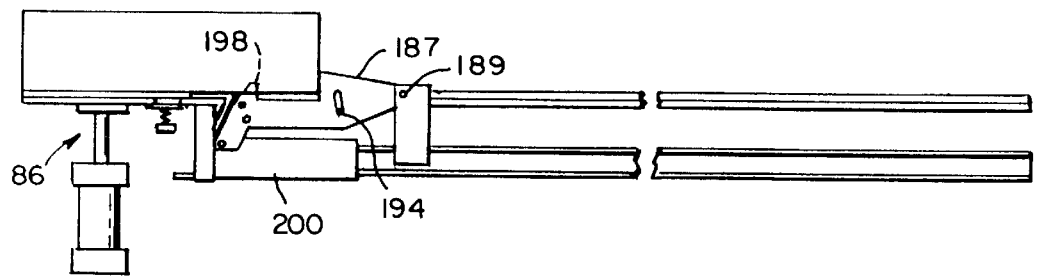
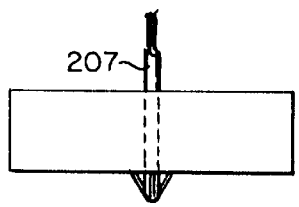
FIG. 21
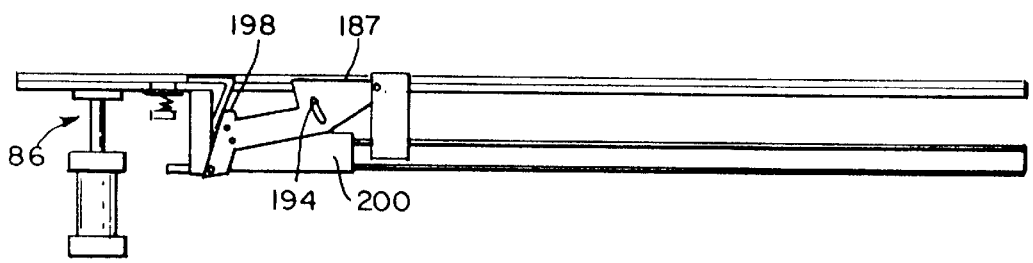

AUTOMATED PHARMACEUTICAL MANAGEMENT AND DISPENSING SYSTEM

PRIOR APPLICATION

This is a division of prior patent application Ser. No. 09/085,968, filed on May 27, 1998, titled: AUTOMATED PHARMACEUTICAL MANAGEMENT AND DISPENSING SYSTEM. Now U.S. Pat. No. 6,219,587 Priority of that application is hereby claimed under 35 USC 120. That application is also hereby incorporated by reference.

TECHNICAL FIELD

This invention relates generally to pharmaceutical management and dispensing systems, and more specifically concerns an automated system for managing the dispensing and inventory of pharmaceuticals or other small medical supplies, the system including patient-specific or drug-specific bin receptacles and related vending carts or cabinets, primarily for use in hospitals, nursing homes and other large medical facilities.

BACKGROUND OF THE INVENTION

Existing hospitals and other large medical facilities typically include a central pharmacy staffed by trained pharmacists and other personnel who fill, by hand, patient-specific prescriptions ordered by individual doctors for their patients being treated at the facility. The pharmaceuticals dispensed by the pharmacy include a wide range of medications, including prescription and non-prescription (over-the-counter or OTC) medications in individual unit-of-use (single use) packages. A typical hospital pharmacy must stock 1500–2000 separate drugs or other line items, of which, on a typical given day, a total of 300–350 different items might be actually used. Certain medical supplies, such as syringes, inhalers, bandages, IV (intravenous) tubes are typically included in such a system.

This institutional-type pharmaceutical-dispensing system, known generally as a "Unit Dose Drug Distribution System", is quite labor-intensive, with each filled medication order comprising individually packaged pills, syringes, patches, etc. in unit-of-use packages. The correct items are hand-picked and placed into each patient's bin (which is hand-labeled with the patient's name), before it is transported in multi-bin groups known as cassettes to and from patient care areas (wards) on transport carts for bed-to-bed dose administration to individual patients by a nurse. The mode and timing of transporting the medications and supplies can vary widely, from being hand-carried to and from patient wards on large cassette transport carts, usually once every so many days (anywhere from daily to seven days) for patient-specific bins, or after-hours doses or starter doses by some other delivery system, such as pneumatic tubes (many times per day) which deliver medications to and from wards without a human carrier, or by semi-automatic vending machines which are refilled by hand one to three times daily.

Typically, when the medication cassettes arrive at the ward, such as on a transfer cart, they are exchanged into and out of mobile carts or stationary cabinets, referred to as medication carts, for later use by the nurses. In such a system, each patient has two bins, one in actual use at the nurse's station (ward) and one being refilled in the pharmacy. In other systems, a single patient bin is labeled and replenished on the ward using a mobile pharmacy cabinet. In nearly every hospital, the patient bins are replenished every one to seven days, with hand-picked/placed patient-specific medication doses.

The carts with the patient bins are usually stored in a medication room at the nursing station in each ward. Typically, the medications are administered by a nurse four times per day. The nurses use a patient profile book to ensure accuracy of medication and administration. The patient profile book is identical to the book used by the pharmacists to fill the patient bins.

The medication carts vary widely in size, arrangement and sophistication, from a very simple cabinet having several shelves for storage of medications for several patients to cabinets having individual bins which are identified according to patient. Typically, medication cabinets are locked and can only be accessed by authorized personnel. In some cases, each individual patient bin or receptacle in the cabinet is individually locked as well.

Such a pharmaceutical system, as indicated above, is heavily labor intensive, particularly for the trained pharmacists, who hand pick and then place the medications in the patient bins, and has a high potential for errors, during the filling of the medication order, during delivery of the medication doses to the ward, and finally during administration of the doses to the patient. The conventional systems are quite slow, taking several hours in some cases to complete a run of medications for an entire hospital, for instance. In addition, the medications already in a patient's bin may be superseded at any time by new orders from the doctor, which can result in confusion as to proper medications for the patient and/or delays in the administration of desired medications.

While it is generally desirable to have patient medications delivered faster in an institutional setting, such as a hospital, i.e. more often than once per day, existing systems are so laborious that such timely deliveries of medications are virtually impossible. It is also well accepted that it would be most desirable to have correct, up-to-date medications delivered just in time (JIT) before they are to be administered to the patient, typically at 8 AM, 12 Noon, 4 PM and 8 PM (hospital times). Other medications for a patient may be provided on an as-needed basis. In addition, it is desirable to have any change in patient medications ordered by a doctor effective immediately, in time for the next medication time. Again, due to cost and the cumbersomeness of existing systems, such a goal has to date been difficult, if not impossible, to obtain.

There have been a few attempts at automating medication dispensing systems in hospitals, but these have not improved overall delivery time significantly, and further are not integrated into an overall system; hence, errors and inefficiencies in the overall system of medication delivery still occur. Centralized pharmacies, where doctors' prescription orders are hand-filled by trained pharmacists, are still the overwhelmingly (95%) used system for hospitals and other large medical facilities.

As indicated above, however, a truly automated and complete medication management and dispensing system is highly desirable for hospitals and other large institutional medical facilities. In such a system, a patient's medication orders will be filled automatically and quickly, and be delivered to the patient ward just before each dosage time. Such a system would also desirably permit the more efficient and more valuable use of pharmacists in a primary role as drug therapy advisers as opposed to filling prescription orders.

Such a system would also correct or significantly improve existing difficulties and inefficiencies in inventory management, permitting appropriate stocking of medications and supplies which move quickly, while not overstocking medications and supplies for which there is little demand. Still further, there is a recognized need and desire in the medical community for an integrated medication management system in which the filling of medication orders and the delivery of those medications to the patient includes multiple safety checks to ensure that the patient receives exactly those medications ordered by the patient's doctor, in the correct dosage, at the right time, and that the medications are those set out in the most recent, up-to-date order of the doctor.

DISCLOSURE OF THE INVENTION

Accordingly, a first aspect of the present invention is an apparatus for automatically dispensing medical elements to an individual bin receptacle, wherein the bin receptacle has at least one individual sector, comprising: at least one vault storage assembly comprising a plurality of storage members for medical elements, each storage member holding a plurality of overpackaged medical elements; means for ejecting the overpackaged medical elements from their associated storage member, in response to a signal command; means for moving the bin receptacle into a medical element receiving position; means for collecting and transferring the ejected overpackaged medical elements into the bin receptacle; and control means, providing signal commands, for controlling operation of the apparatus.

Another aspect of the present invention is a method for dispensing medical elements for a patient into an individual bin receptacle and subsequent delivery of said bin receptacle to the patient for use of the medical elements, comprising the steps of: receiving selected medical element information for a patient, such as from a hospital computer; transferring said medical information to a medical elements dispensing apparatus; maintaining a selected number of medical elements in the medical elements dispensing apparatus; moving a bin having at least one sector therein into the medical elements dispensing apparatus, wherein each bin is uniquely identified with a patient; automatically obtaining selected medical elements from storage members therefor in the apparatus and moving them into the bin; moving the bin containing the medical elements away from the medical elements dispensing apparatus; moving the bin containing the medical elements to the vicinity of the patient associated with the bin; and correlating the bin and selected medical elements therein with the patient to ensure a match prior to the patient receiving the medical elements.

Another aspect of the system of the present invention is a system for automatically controlling the use of medical elements in a health care facility, comprising: means for storing information concerning prescribed medical elements, including medications, for a plurality of patients at a health care facility; at least one vault storage assembly comprising a plurality of storage members for medical elements, each storage member holding a plurality of packaged medical elements; means for moving an individual bin receptacle for holding medical elements, the bin receptacle having an identifying indicia thereon which is associated with one particular patient, into a medical-dispensing apparatus, said medical-dispensing apparatus including means for dispensing prescribed medical elements into the bin receptacle in accordance with the information from the information-storing means; means for moving the bin receptacle with the prescribed medical elements therein out of the medical-dispensing apparatus; means for delivering said bin receptacle to the vicinity of the patient; means for correlating the identification indicia on the bin with identification indicia on the patient to ensure a match prior to the patient receiving the medical elements; and means for automatically controlling the operation of the vault storage means, the receptacle moving means, and the bin receptacle moving means in accordance with the control program and the information storage means.

A further aspect of the system of the present invention is a medication cart for securing and dispensing medical elements, including medications, comprising: a cart housing; rotatable support means within the housing for at least one stack of medical element bins, each bin being divided into a plurality of sectors; means for indexing and tracking rotation of the bins so that the rotational position of the bins relative to a home position is always known; means for preventing unauthorized access to the interior of the housing of the bins; means for stopping the rotatable support means, after rotational movement thereof has been initiated by an operator, at a rotational position such that a bin is accessible and the housing is open; and means, in response to a command signal, for opening the housing to permit access to the desired bin and any medical elements therein.

Another aspect of the system of the present invention is an overjacket package for unit-of-use medical elements, including medications, such that the medical elements can be conveniently dispensed from an automatic element-dispensing apparatus into individual bin receptacles, comprising: a closed package member having an interior for holding a unit-of-use of selected medical elements; and at least one line of perforations in the package member which extends around a substantial portion of the package member, such that the package member may be readily broken apart along the line of perforations to provide access to the unit-of-use medical element contained therein.

BRIEF DESCRIPTION OF THE DRAWINGS

FIG. 4 is a top view of the patient bin of FIG. 2.

FIG. 5 is a bottom view of the patient bin of FIG. 2.

FIG. 6 is a side view of the patient bin of FIG. 2.

FIG. 11 is a side elevational view of the download elevator portion of the system of the present invention.

FIG. 12 is a side elevational view showing the download elevator of FIG. 11 in a different operating position.

FIGS. 19–21 are side elevational views showing the structure for moving a filled patient bin from the central collator to the upload elevator.

BEST MODE FOR CARRYING OUT THE INVENTION

Figure 1:
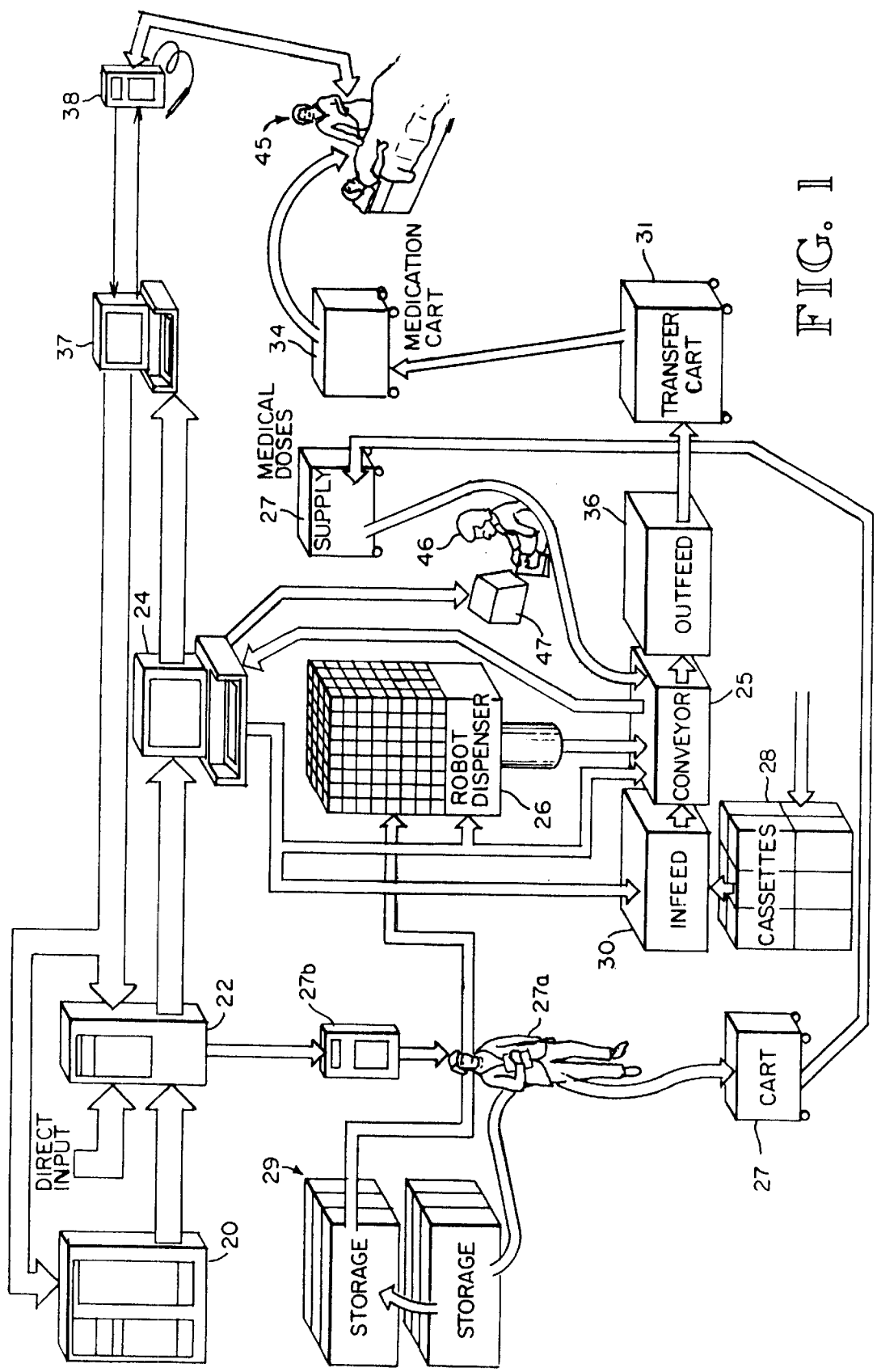
FIG. 1 is a pictorial overview of the system of the present invention.
Figure 2:
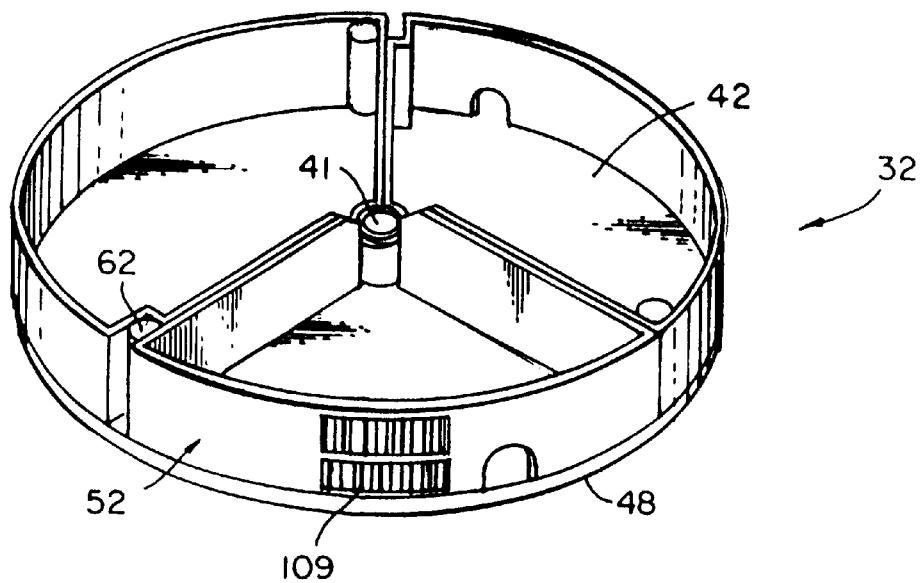
FIG. 2 is a perspective view of a patient bin used in the system of the present invention.
Figure 3:
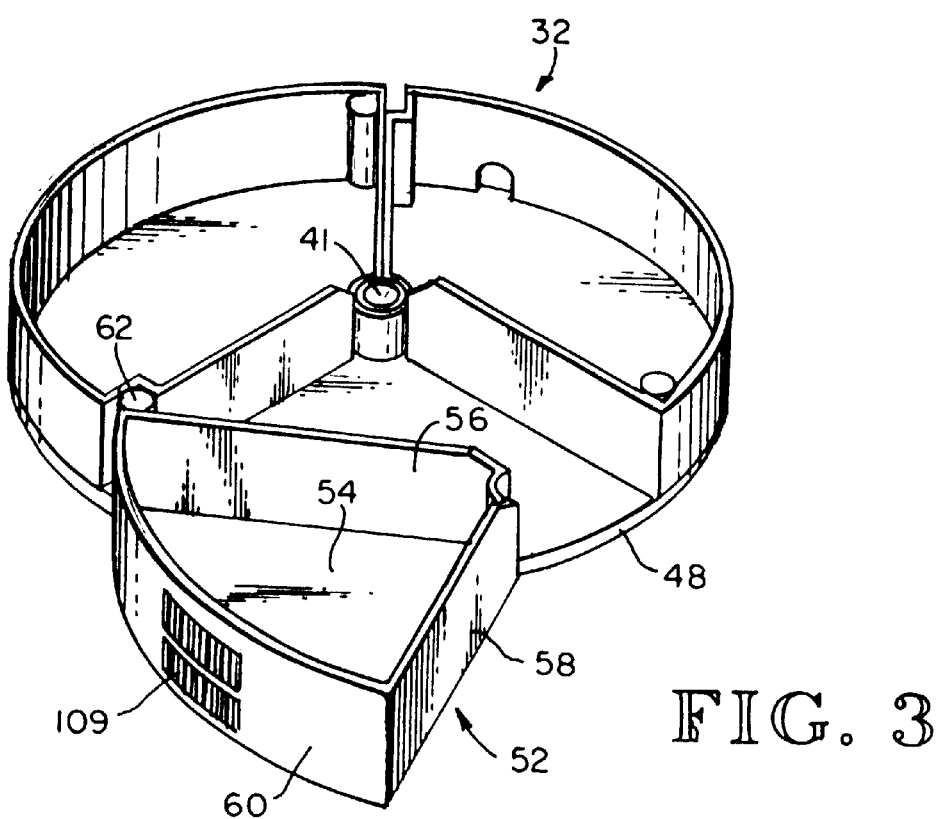
FIG. 3 is a perspective view of the patient bin of FIG. 2, with one sector being rotated outwardly.

FIG. 1 shows an overview of the complete closed system of the present invention. Supporting the system of FIG. 1 will be one or more central national packaging and distribution centers, which receive unit-of-use doses of all of the desired medications from the various drug manufacturers, either directly or through wholesalers. In addition to medications, certain medical supplies, such as syringes, sponges, clamps, etc., are obtained and are included in the present system. However, for simplicity of explanation, the focus of the present description will be on medications, both prescription and non-prescription (over-the-counter). It should be remembered, however, that medical supplies can and typically will be included in the present system. The term "medical elements" as used hereinafter is intended to include both medications and medical supplies.

The national packaging and distribution center will likely be located at one or more national transportation hubs, for convenience of distribution of the medications to the hospitals and other facilities which use the automated medication management system of the present invention. Such a center might be located, for instance, in Memphis, Tenn., close to the central Federal Express facility, and/or in Louisville, Ky., close to the central UPS facility.

The packaging and distribution center, which will also include a bar coding capability, will order medications from the various drug manufacturers, either directly or from wholesalers, in accordance with a computer controlled inventory system, which will continuously track and forecast the volume of individual medications supplied to the various hospitals and other facilities. Because the system tracks medications to the patient-specific level, a report will allow analysis of a doctor's prescribing performance quality in terms of proper drug, dose, dosage form, frequency of use, duration of therapy, drug combinations, etc.

At the packaging center, the typically foil-wrapped or blister-packed unit-of-use doses provided by the various drug manufacturers will be bar-coded, overjacketed (with a package), and then sleeved by placing each separate pill, syringe, liquid dose, etc. into one of several different, uniform-size overjacket package. In some cases, an overjacket container may not be necessary, due to the configuration of the unit-of-use package. Each unit-of-use overjacketed, bar-coded package is also typically labeled with human-readable information, identifying the medication name, dosage form, strength, lot number and expiration date. While the present invention is described as using a bar code indicia, it should be understood throughout this explanation that other identifying indicia could be used.

In the present system, there are seven different uniform box sizes, each size designed to accommodate any of a multiplicity of different unit-of-use doses of medications/supplies. For instance, a 1"×5"×0.5" overjacket could contain various oral solid medications, suppositories, unit dose eyedrops, ampoules, and the like. Other sizes can be used for different size syringes, while another size can be used for oral liquid doses and powders. Typically, there is one large size box for bulky items. An arrangement of breakaway perforations and cutouts is used to permit easy "pop-open" access to the interior of the boxes, as explained in more detail below.

The uniform size and configuration of the overjacket packages, together with a relatively small number of possible different sizes (i.e. seven), are important to the system of the present invention, although the number of different sizes of overjackets can be varied. For a particular size, however, the packages are all identical in construction, size and configuration, adapted to be readily automatically ejected from a storage member portion of the dispensing system, which is described in more detail below.

A plurality of overjacketed packages, each of the same size and containing the same medical element, is placed in a sleeve member which is adapted to be fitted into a cartridge-like member in the storage member portion of the dispensing system. Uniform packaging is quite important to the operation of the present system, as it significantly reduces the effect of the current wide variability of size and configuration of unit doses of medications, which currently include literally hundreds of different shapes and sizes that are quite difficult for high speed robotic systems to otherwise accommodate.

The system of the present invention includes a substantial amount of data generation and flow. It is in essence a "closed loop" system in which information obtained is used to alter the operation of the system. Referring to FIG. 1, in a hospital or other large facility, a patient is first assigned a patient I.D. number, in bar code format or other identifying indicia, which is provided on a band attached to the wrist (typically), and a bed assignment by a hospital computer 20. Typically, this is done in the emergency room or the admitting department. This information is provided to a pharmacy central computer 22. Doctors' prescriptions are typically entered directly into the pharmacy central computer 22 by a pharmacist or pharmacy technician or indirectly by a ward-based computer, lap-top or internet computer device.

The prescription information, the patient I.D. and the bed assignment are then provided to a dispensing system control computer 24, sometimes referred to hereinafter as the robot control computer, which controls a multi-vault medication-dispensing system, referred to generally as a robot dispenser 26. The robot dispenser 26, consisting of five dispensing vault assemblies in the embodiment shown, each with its own microprocessor control, as described in detail below, will typically be located in its own room and is controlled by command signals to and from the robot control computer 24 and the microprocessors on board each vault assembly.

The robot dispenser 26 in the embodiment shown has been stocked with overjacketed packages containing unit doses of over 500 different medications, which comprise approximately 90–98% of the daily volume of medications (fast movers). Overjacketed packages are stored in multi-package bar-coded sleeves. The sleeves serve as disposable carriers which are thrown away after they are used to load their packages in the robot dispenser, leaving behind the individual overjacket packages inside bar-coded cartridge members, which are in turn mounted to their own bar-coded cartridge holder ejector assembly. The remaining 1500+ medications (slow movers) are arranged on shelves around the periphery of the room. Both fast and slow mover medications have a bar-code identification which is imaged (overseen) by the hospital computer 20.

In the automatic filling of prescriptions for patients, medication receptacles, known as bins, are delivered to the input side of the dispensing system in the form of a succession of stacks of bins 28—28, known as cassettes, with each cassette 28 comprising a stacked plurality (typically 8–20) of individual bins. Three types of sectioned bins are generally used, as discussed hereinafter, although other bin arrangements are possible. The three bins currently in use have three, five or ten sections. Each cassette presently includes only one type of bin, although a mix of bin sizes is possible. The stacked cassettes are pre-designed to be either patient-specific or medication-specific by the system software.

Each bin has a permanent label with a bar code identifying the bin. Only three and five sector bins are designated as patient-specific, whereas any of the three can be designated as medication-specific. In ten-sector bins, each sector typically (but not necessarily) is restricted to contain only a single unit-of-use package. In three and five sector bins, each sector may contain a plurality of such packages. If the bin is configured as a patient-specific bin, then the particular bar code on the bin is associated with a particular patient's bar code upon admission of that patient to a nursing ward and then is dissociated from that patient upon discharge or transfer from the ward. During the patient's stay in the facility, the patient is linked with a particular bin or bins through software control.

The cassettes are placed on an infeed system, in which individual bins are one-by-one first read and then separated from the remainder of its cassette, shown generally at 30 (FIG. 1), as described in more detail below. The obtained information (identification of both the cassette and the bin) is supplied back to the pharmacy central computer 22, which checks and communicates current up-to-the-minute orders and nurses' use records and/or bin use records to determine bin refill needs. The bins are then moved one-by-one to the central dispensing apparatus (robot dispenser) 26 by means of a conveyor shuttle system, shown representationally at 25, where they are loaded with the desired "fast mover" medications for that patient bin or medication bin by the dispensing apparatus 26. The robot dispenser is filled with "fast mover" medications from storage 29 during off hours. The filled bin is then moved by the conveyor shuttle system away from the dispensing apparatus 26.

"Slow mover" medications (if any) are supplied to the bin from a semi-automatic (or automatic), computer-assisted supplemental dose cart shown generally at 27. The conveyor shuttle system stops the bin at cart 27 only if supplemental medications are needed. Information concerning the slow mover medications is provided by pharmacy central computer 22 to a technician 27a, who pre-loads cart 27 from storage 29 for each complete run of the robot dispenser 26, with the aid of a hand-held scanner 27b. The cart is then moved to its operating position adjacent the conveyor shuttle system, following the robot dispenser 26. A technician 46 adds the additional medications from the cart 27 to the bin at this point, with the aid of a monitor 47, connected to the pharmacy control computer 22.

The bins are then moved to an outfeed system 36, where successive bins are reassembled into filled-bin cassettes. The completed cassettes at the outfeed system have the same set or family of patient bins as the cassettes at the infeed system, even though each cassette is briefly disassembled and then reassembled during the bin-filling process. The cassettes are then manually moved away from the robot assembly to a transfer cart shown at 31 and then moved manually by a human courier to a medication cart shown at 34, which is always left at and permanently assigned to a specific nursing station/ward.

Once the bins have arrived at the nursing station, the nurse and the cart courier will together enter security codes into the transfer cart and medication cart keypads, which will result in the unlocking of both carts to allow cassette exchanges, by the nurse or cart courier, as directed by scanning menus and verified by bar-code scans, followed by nurse and courier PIN (personal identification numbers) to activate locks on the carts. In the cassette exchange, the cassettes on the medication cart will be moved by hand to the transfer cart, and the filled cassettes on the transfer cart moved to the medication cart. Any unused medications returned to the pharmacy in the returned cassettes are either disposed of or returned to the dispensing system. Thus, neither the nurse nor the courier can access either cart alone, with each party thus serving as a witness to the exchange of cassettes.

At each of the four standard hospital dose times at every nursing station (8 AM, 12 Noon, 4 PM and 8 PM), a nurse 45, through a hand-held scanner 38, will scan her ID badge and enter her PIN to release the wall-locked medication cart to the particular nurse who rolls the cart to each patient (e.g. room to room or bed to bed), in any order. In one variation of the present invention, the medication cart may not be locked to the wall. Once at the patient's side, the nurse will scan the patient's bar code ID on his/her wristband and read the scanner screen for prescription-related instructions, if any, prior to returning to the medication cart. Information is provided to and received from scanner 38 by a nursing station computer 37, which is also in data communication with the pharmacy central computer 22. Information is also recovered from the robot computer 24. Such additional instructions may include directions to obtain the patient's pulse, blood pressure, temperature, etc. These results are then entered into the scanner keypad, which in turn will quickly give dosing clearance or warn the nurse when she returns to the cart and obtains related doses.

After scanning the patient's ID bar code and entering any data, the nurse 45 returns the scanner 38 to its cradle on the medication cart 34. Access is provided to the correct sector of the patient's bin only (as more fully explained below). The nurse removes the medications in the sector and scans the bar code thereon to receive clearance to administer the medications. The nursing station computer 37 immediately receives the patient medication information results for each patient in real time from the pharmacy control computer 22, which is connected to the hospital computer 20.

After each patient is medicated, the information in scanner 38 is downloaded into the nursing station computer 37, and/or the hospital computer 20, from which it is directed back to the pharmacy control computer 22. Data from computer 37 could also be provided directly back to the pharmacy control computer. The hospital computer 20 maintains a continuously updated, complete database of dose inventory, whether present in the pharmacy, the robot dispenser 26 or the individual bins. The system thus maintains a "closed loop" of information and medications and the patient's use thereof. All patient medications and all medication inventory are accurately tracked and accounted for at all times.

All used cassettes are returned to the robot dispenser for the next round of filling by means of the nurse/courier exchange process described above. The use of this process will vary, from as many as four times per day to once every other day in some facilities.

The medications and other medical supplies in the present system are dispensed into and then administered to patients from individual bin receptacles, and in particular, specific sectors of the bins. The bin receptacles may either be patient-specific, i.e. a specific bar-coded bin containing each patient's medications or other medical supplies, or drug/supply-specific, i.e. a bin which contains combinations of preselected drugs or other supplies for use by the nurses but which are not specific to a particular patient. Drug/supply-specific bins, for instance, can be used for selected narcotic drugs, "first dose" drugs, and newly-ordered after-hours drugs, emergency room doses, operating room medications and other applications.

As discussed briefly above, the patient-specific bins typically are divided into either three or five parts or sectors, depending upon the facility, while the drug-specific bins typically, but not always, have more sectors, i.e. ten. For illustration purposes, a three-sector patient-specific bin will be described in detail. These bins will typically be used in hospital settings, where four, three or two times per day a cassette delivery occurs. A five-sector patient-specific bin will typically be used in a facility like a nursing home, where the bins are filled and delivered once daily. In hospitals, where prescriptions and patient movement is far more complex, the three-part bin can be used for medication delivery just before each time the medications are to be administered (i.e. JIT, just in time).

The bins, regardless of the number of sectors, are typically circular in configuration, having a diameter and height which can vary, but in the embodiment shown are approximately 14.25" in diameter and 2⅝" high. FIGS. 2–6 show a three-sector bin 32. While the bin 32 in this embodiment is circular in configuration, it should be understood that other configurations, including square, rectangular, hexagonal, etc., could be used. Bin 32 includes a base portion 39 (FIG. 6). The base portion 39 includes a cylindrical opening 41 at the center thereof, approximately 1½" in diameter.

In a lower surface 42 of base portion 39 are two spaced grooves 43 and 44. Grooves 43 and 44 extend parallel to each other across the lower surface of the base portion of the bin. The grooves are positioned an equal distance from central opening 41. One end of each of the grooves adjacent the peripheral edge of the base portion flares outwardly such that the entrance portions 43a and 44a to the grooves at that point are approximately 3" wide, with the entrance portions curving inwardly over a short distance to the remaining portion of the grooves. The flared entrance portions, respectively, of the respective grooves permit the bin to be slightly misaligned initially relative to the spaced tracks on which it will move within the dispensing system. A cutout portion 119 is also located in the lower surface 42, the function of which is discussed in more detail below.

Attached to the top of base portion 42 by means of screws or the like is a flat plate 48. Upstanding from plate 48 are three pie-shaped sector containers or drawers 52—52. Sector drawer 52 includes a bottom plate 54, side walls 56 and 58 and a curved outer wall 60 connecting the side walls at the periphery of plate 48. The drawer is open at the top. The rear portion of each drawer, defined as the wall portion between side walls 56 and 58, is configured to mate with the central opening 41 in the base of the bin. In the embodiment shown, each sector drawer can swivel outwardly about a vertical rod 62—62 positioned adjacent one corner of each container at the periphery of plate 48. An alternative embodiment is a pull-out drawer with a straight spine on the underside thereof which mates with a groove in the base portion of the bin.

The swivel arrangement of FIGS. 2–6 permits sector drawers 52 to be conveniently and simply rotated in and out relative to the remainder of the bin. It should be understood, as indicated above, that other sector divisions and bin configurations can be used. For instance, the above description concerns a three-sector bin, with two sectors being 144° wide and with the other remaining sections being 72° wide (FIG. 4). As stated above, this configuration is convenient for a hospital patient. However, other facilities, such as nursing homes, may require a five-sector bin, each sector in that case being 72° wide.

In addition, a drug/supply-specific bin configuration might involve as many as ten sectors. Other arrangements and configurations can be used as well. As indicated above, however, the basic concept of the individual bin receptacle, with multiple separate sectors for medications, is an important part of the overall system of the present invention, particularly in terms of reliably and quickly dispensing and administering medications and medical supplies.

The following paragraphs describe the portion of the system mentioned above in which the individual receptacles or bins are filled in accordance with a known medication regimen for the particular patient associated with the bins. For purposes of illustration, a single bin will be followed during a normal filling process.

The receptacle described, again for purposes of illustration, is a three-sector bin, with the complete system being located at a typical hospital facility. It would thus be anticipated that the bin be filled by the robot dispenser just prior to each medication time, e.g. shortly before 8 AM, 12 Noon, 4 PM and 8 PM, with prompt delivery thereafter to the nurse's station by means of the transfer cart. One of the sectors will be filled with medication due to be administered at the imminent regular medication time, e.g. 8 AM. The second sector is for as-needed medications, such as aspirin for pain, etc., while the third sector is for any of a variety of scheduled doses to be given after the imminent regular medication time but before the next cassette exchange occurs. The largest sector is selected by the software in the robot control computer for the largest volume of doses to be stored, whether they are the scheduled doses or the "as-needed" doses.

Figure 7:
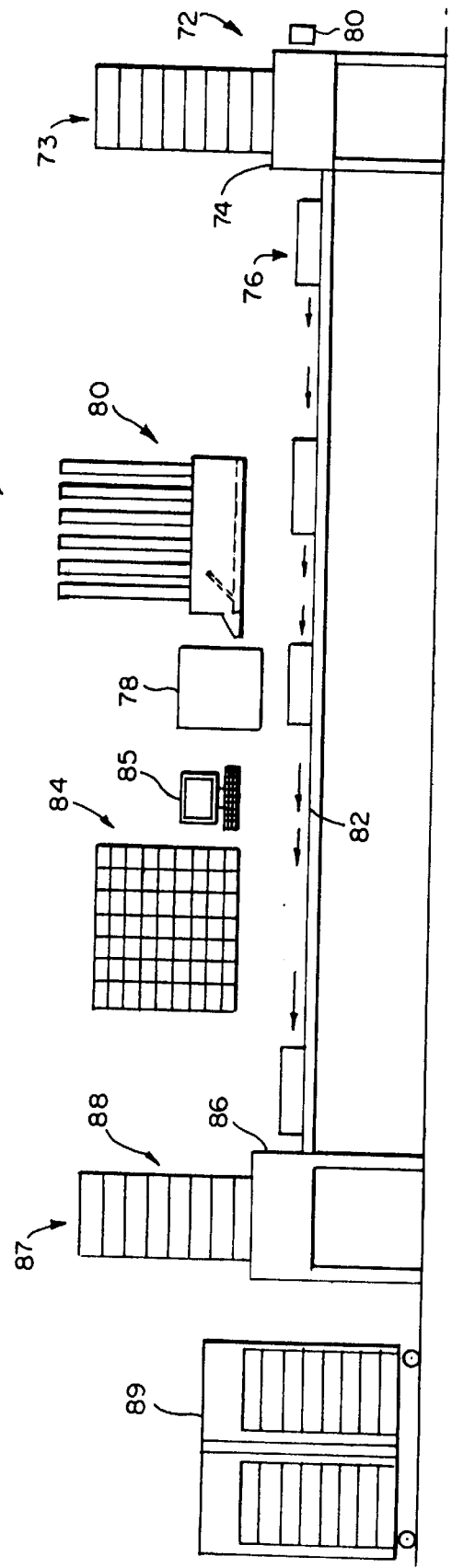
FIG. 7 is a simplified elevational view of the system of the present invention.
Figure 8:
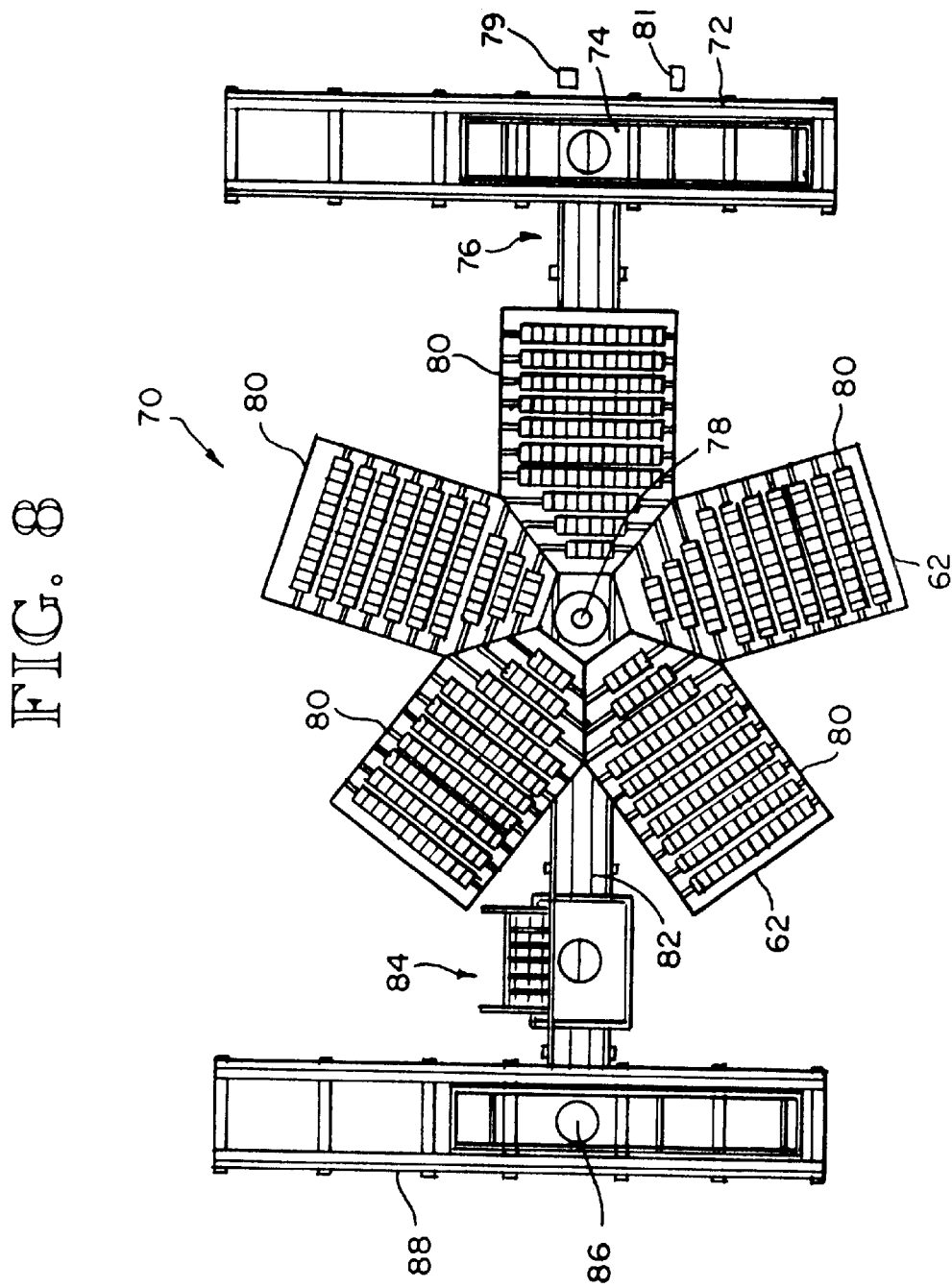
FIG. 8 is a simplified top plan view showing the system of the present invention.

FIGS. 7 and 8 show a general overview of the bin-filling system 70 of the present invention. Generally, the bin-filling system 70 includes in its major sub-sections an infeed conveyor 72 for the bin cassettes 73, a download elevator 74 which disassembles the incoming cassettes, and an infeed shuttle assembly 76, which feeds the bins to a filling position beneath a central collator assembly 78. Sensors 79 and 81 in FIG. 8 maintain control over the progress of the bin cassettes and the individual bins. Medications are provided to the collator assembly 78 by five separate medication vault assemblies 80—80, each of which is movable on wheels and tracks relative to the collator assembly 78. These vaults can be stored among any number of other mobile vaults located nearby. One or more of the vaults could be fixed in place with the collator assembly.

As will be explained in more detail below, the patient bins are filled by operation of the collator assembly, by dropping medications through a trap door at the bottom of the collator assembly. The bin is automatically moved away from the collator assembly 78 by an outfeed or exit shuttle assembly 82, past a supplemental dose (SD) cart 84 (with a keyboard, mouse and touch screen 85), to an automatic upload elevator assembly 86 and an outfeed conveyor assembly 88. The reassembled cassettes 87 are then manually moved to a transfer cart 89 and then to a medication cart (not shown) which is kept at all times in the patient ward or area, from which the medications are dispensed. The medication cart is moved from bed to bed. Each of the above assemblies will be described in more detail in turn.

Figure 9:
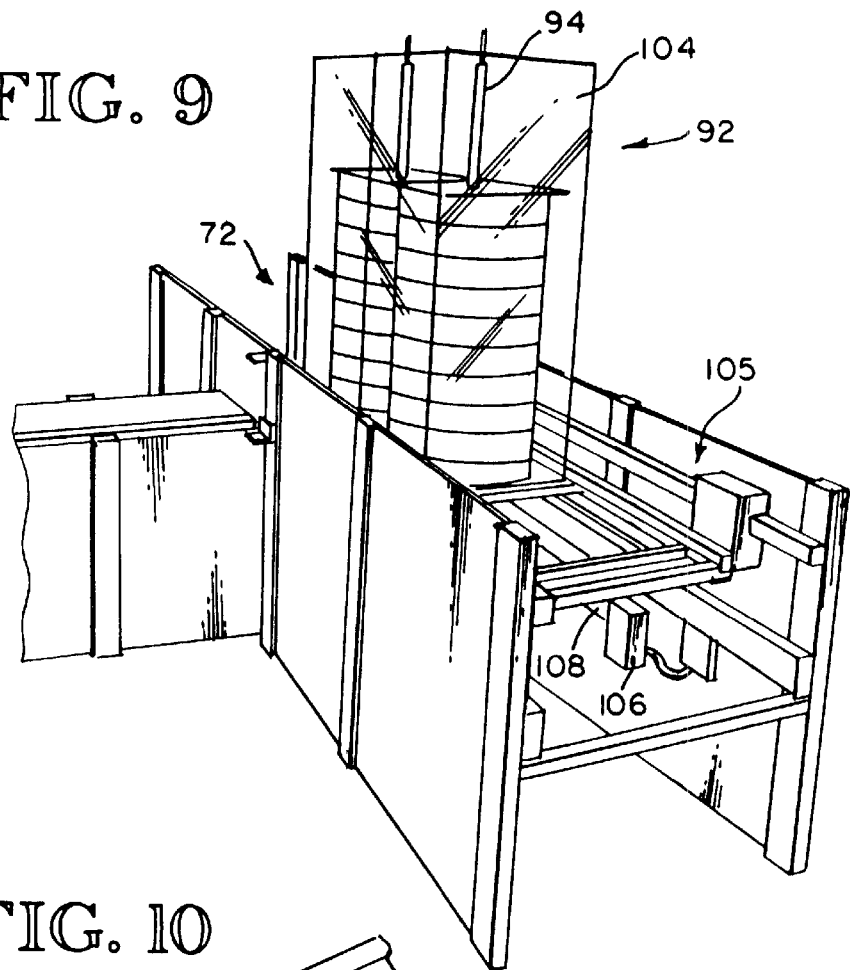
FIG. 9 is a perspective view showing an infeed conveyor portion of the system of the present invention.

As discussed above, a significant aspect of the system of the present invention is that the individual patient bins are transported to and from the bin-filling assembly in the form of successive stacks of patient bins, each referred to as a cassette. Each cassette comprises a plurality of patient bins, drug/supply bins or other bin types. In the embodiment shown, referring to FIGS. 9 and 10, cassettes shown generally at 92—92 on infeed conveyor 72 comprise a total of ten individual patient bins, although the number of bins could be varied. Referring to FIGS. 9, 11 and 12, each cassette includes a center latching pole assembly 94 upon which the individual bins are centered and nested together with adjacent bins. Each cassette assembly includes a housing 104 which in the embodiment shown is four-sided and clear plastic, enclosing the stack of bins therein. The bottom of housing 104 is open.

The latching pole assembly 94 is suspended from the top of housing 104. As shown in FIG. 11, the latching pole assembly 94 comprises an inner pole 96, which has three spring-biased ears 98—98 near a lower end thereof, the ears being biased by springs into an outwardly directed position (as shown) in which the outer edge of the ears extend beyond the peripheral edge of opening 41 in the patient bins, so that the ears support (initially) a number (e.g. ten) of patient or drug/supply bins above them. However, when the ears on the latching pole are moved inwardly against their spring bias, a bin can move downwardly on the pole assembly over the ears.

The central cylindrical opening and the configuration of the rear portion and adjacent sections of the side walls of each bin are designed so that the ears will spring back in time to catch the next bin and the bins above the next bin after releasing the bottom-most bin onto the download elevator. The latching pole assembly includes a hollow outer pole 101 which fits over the inner pole 96 and is movable relative thereto by a spring connection (not shown) between them at the bottom thereof. The outer pole 101 includes three openings near the lower end thereof, through which ears 98—98 of inner pole 96 extend. When outer pole 101 is moved upwardly against the spring connecting it to the inner pole 96, the lower edges of the openings in the outer pole 101 act against the ears 98—98 of the inner pole, forcing them inwardly toward the surface of the inner pole, in which position, as indicated above, bins may pass freely, one at a time, over the ears and move off of the pole assembly.

Returning to FIGS. 9 and 10, in operation of the apparatus, the infeed cassette conveyor 72 of the bin filling assembly moves the bin cassettes one by one into proper position over the download elevator 74, which removes and lowers the bins one by one from the bottom of the stack to the infeed bin shuttle assembly by acting on the latching pole assembly in the manner described above. The infeed cassette conveyor 72 includes a frame 105 (FIG. 9) having a moving portion which is arranged to receive successive cassettes and maintain them in a spaced relationship, so that the position of each cassette on the infeed conveyor can be accurately known relative to the download elevator.

As discussed above, the individual cassettes are moved by hand from a transport cart, in the embodiment shown, onto infeed cassette conveyor 72, in an in-line arrangement. (Two cassettes are shown in FIG. 9, although it should be understood that additional cassettes could be accommodated on a larger conveyor.) It should be also understood that this transfer of the cassettes onto the infeed cassette conveyor can also be done automatically. Once the cassettes are mounted onto the cassette conveyer 72, they are automatically moved to a correct position, in due time, over the download elevator. The conveyor is moved by a motor 106 and a lead screw assembly 108. The motor 106 is controlled by electrical signals from the robot computer 24.

Knowledge of the location of individual bins in each cassette and control over the individual bins throughout the bin-filling process is achieved through the use of bar code identification, as discussed briefly above. A bar code number is placed on all of the key components of the system, including individual bins, individual bin sectors, packaged medications, the transfer cart and the various packaging components. Bar code identifications 109 are shown, for instance, on the bins illustrated in FIGS. 2, 3 and 6. They are typically positioned on the vertical sides of the bins. RF chips embedded in the base of each bin would be an alternative arrangement.

As also discussed above, a bar code is assigned to each patient when they are admitted to the hospital. The patient wears a wristband with the assigned bar code number; a bar-coded medication bin is thereafter associated with that particular patient by means of software control. With the aid of fixed and portable scanners at various points in the system, the use of bar code identification permits exact control over the location of the individual bins, bin sectors and the medications that are loaded into them. While the use of bar codes is discussed throughout the following description, it should be understood that other identifying indicia could be used.

Figure 10:
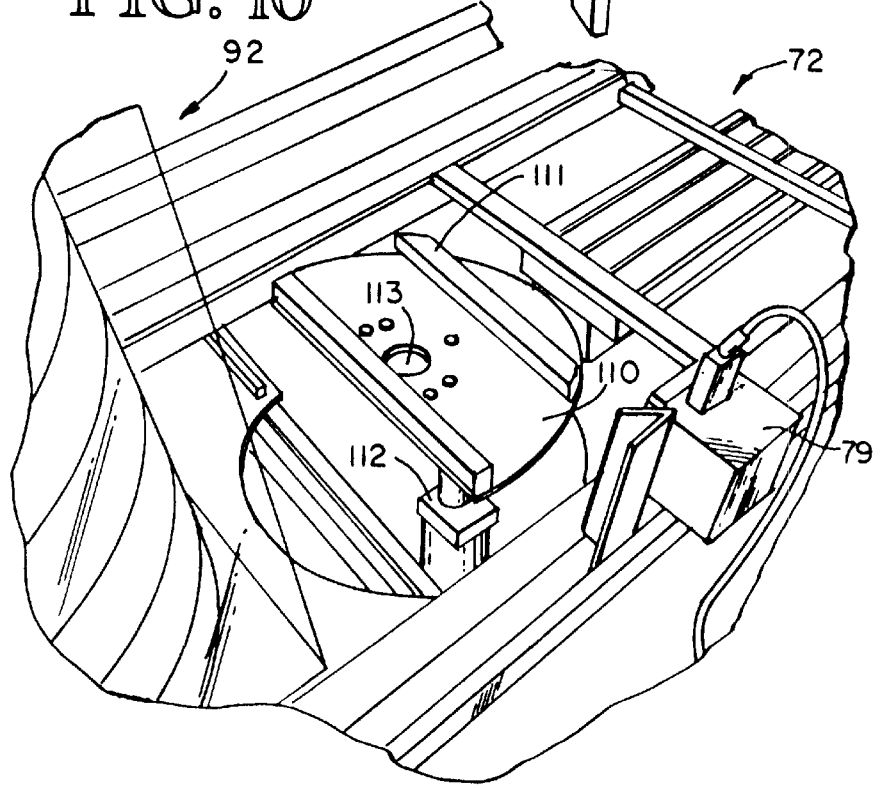
FIG. 10 is a perspective view showing a portion of the structure of FIG. 9.

When a full cassette is moved into proper position on the download elevator 74 along the infeed conveyor, the bar code on the lowermost bin in the cassette is read by a mounted scanner 79 (FIG. 10). Other scanners, such as scanner 81, which can be used for example to verify the position and movement of the cassettes, could be positioned at other points along the infeed conveyor. The bar code information is provided to the robot computer 24 so that it knows which bin is on the download elevator and thus which bin is about to be moved through the bin filling process.

As shown in FIG. 10, the bins will all have a selected orientation, in which the grooves 43, 44 on the bottom of the bin are aligned with matching spaced raised alignment elements or tracks 111 on the upper surface of an upper elevator plate 110 of the download elevator, elevator plate 110 being movable vertically by means of a pneumatic powered member 112. A stepper motor could be used as an alternative. Elevator plate 110 has an opening 113 in the middle thereof through which the bottom of the latching pole assembly extends. As shown in FIG. 11, a short distance beneath the opening 113 in the upper elevator plate 110 is a smaller support plate 114 mounted by a spring and bolt arrangement 115, to upper elevator plate 110. The lower end of latching pole assembly just rests against support plate 114 when a cassette is in the correct position and the elevator has been raised to its operative position for removal of the lowermost cassette.

The slight further raising of support plate 114 (when plate 110 has been moved by the pneumatic member 112) moves outer pole 101 upwardly, which results in ears 98—98 on inner pole 96 being moved sufficiently inwardly, as discussed above and shown in FIG. 12, to allow the lowermost patient bin to move downwardly over the ears. The upper elevator plate 110 is then lowered slightly, lowering the outer pole 101 such that ears 98—98 are free to spring out again underneath the next lowermost bin when the lowermost patient bin clears the ears. When the lowermost bin completely clears ears 98—98 and they have sprung out, the next bin is caught and held on the pole assembly, as are all the bins above it. Control over the movement of the elevator assembly results in only one bin at a time moving off the latching pole.

Sensors (not shown) are located to sense the movement and alignment of the lowermost bin as it moves down and off the latching pole assembly, away from the remaining bins and into its indexed position on the upper elevator plate. The sensors thus confirm the release of one bin (the one that has been read by scanner 79), as well as ensuring that one (and only one) bin has been released from the latching pole assembly. This is accomplished by a feedback loop arrangement with automatic corrective action and reports to the operator.

Figure 13:
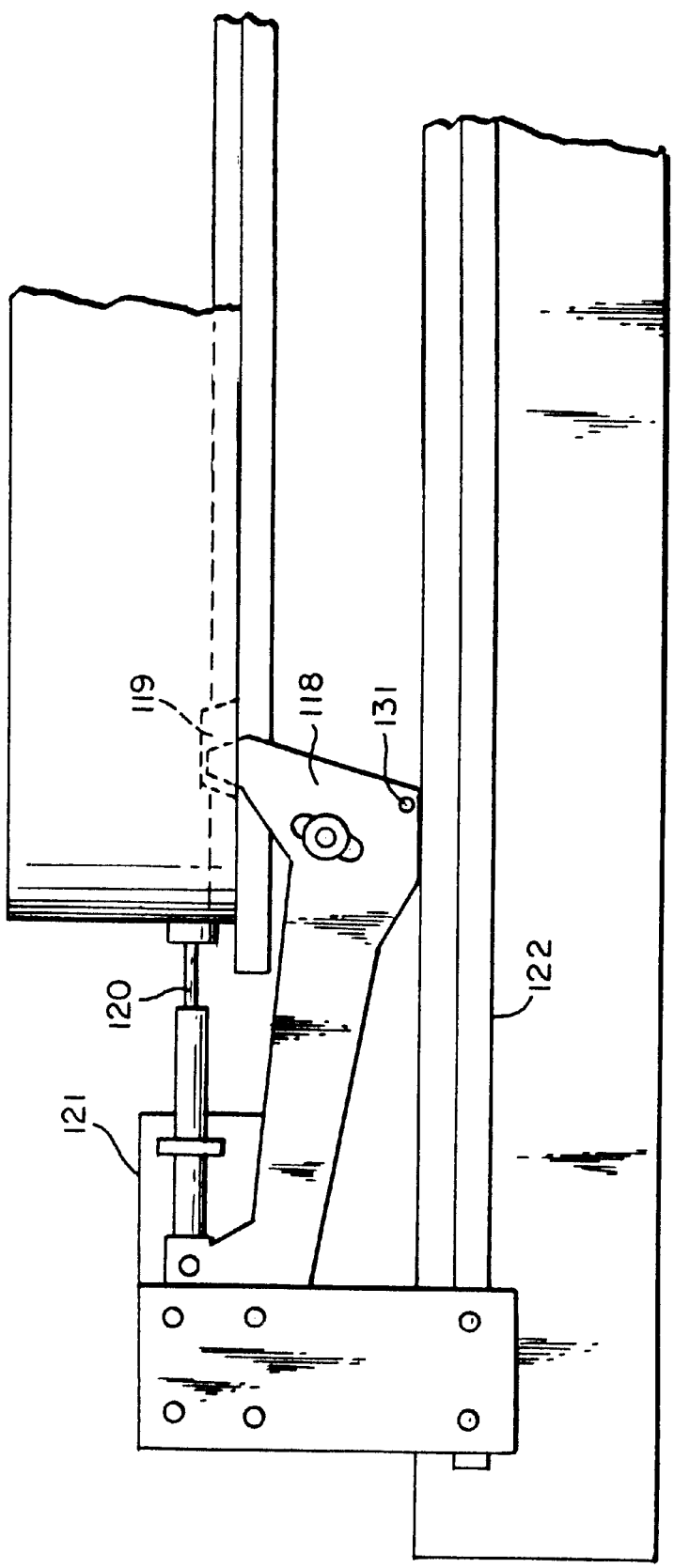
FIG. 13 is a side elevational view showing the carrier which moves the bin from the download elevator to the central collator assembly portion of the present invention.

The released bin is now in position to be secured onto and moved by the infeed bin shuttle assembly 76 which extends from the infeed conveyor to the robot dispenser. As the released bin is lowered away from the remainder of the bins in its cassette and the download elevator moves downwardly to a preselected position, referring to FIG. 13, a carrier latch portion 118 of a carrier assembly 121 hooks onto the bin in cutout portion 119 in the bottom surface of the bin. An air-filled piston 120, which is also part of carrier assembly 121, in operation forces the bin against a protruding edge of latch 118. At this point, the bin is moved away from the download elevator 74 by carrier 121, with the carrier moving pneumatically by means of an associated air cylinder (not shown) mounted on the bin infeed shuttle assembly frame.

Carrier assembly 121 is mounted on and moves along a horizontal guide 122, which in turn is mounted on the infeed bin shuttle assembly frame, to its destination directly beneath a pneumatic trap door of collator assembly 78. Extending between download elevator 74 and collator assembly 78 are a pair of spaced horizontal tracks 122, which are approximately 7" apart. The bin is initially oriented in its cassette on the download elevator such that the flared openings 43a, 44a of the grooves on the lower surface of each patient bin are aligned generally with said two spaced tracks which are a part of the infeed shuttle system. Upon a control signal from the robot computer 24, the carrier assembly 121 and the bin are moved along the spaced tracks by an air cylinder.

As the bin is about to reach collator assembly 78, a forward pair of centering pins 130—130 (FIGS. 14 and 15) pop out at the far side of the collator assembly, acting, in effect, as catching elements for the moving bin. As the bin approaches the forward centering pins 130—130, the carrier latch 118, which is hooked to the bin, moves past a cam (not shown) mounted on the supporting frame, the cam coming into contact with an extending horizontal pin 131 on the latch. Further movement of the patient bin causes the carrier latch 118 to rotate downwardly, releasing the bin. Piston 120 continues to apply pressure against the bin, forcing the bin against the centering pins 130—130. The air cylinder at this point reaches the end of its stroke. This is determined by sensors 132 mounted on the supporting frame for the infeed shuttle assembly.

A signal from sensors 132 results in a rear pair of centering pins 133—133 popping up at the rear of the bin, thereby capturing the bin between the two sets of pins 130 and 133, in correct position beneath collator assembly 78. The infeed cylinder then quickly moves back to its original position, in proximity to the download elevator, taking the carrier 121 therewith, ready for operation on the next bin to be removed from the cassette on the download elevator.

Figure 16:
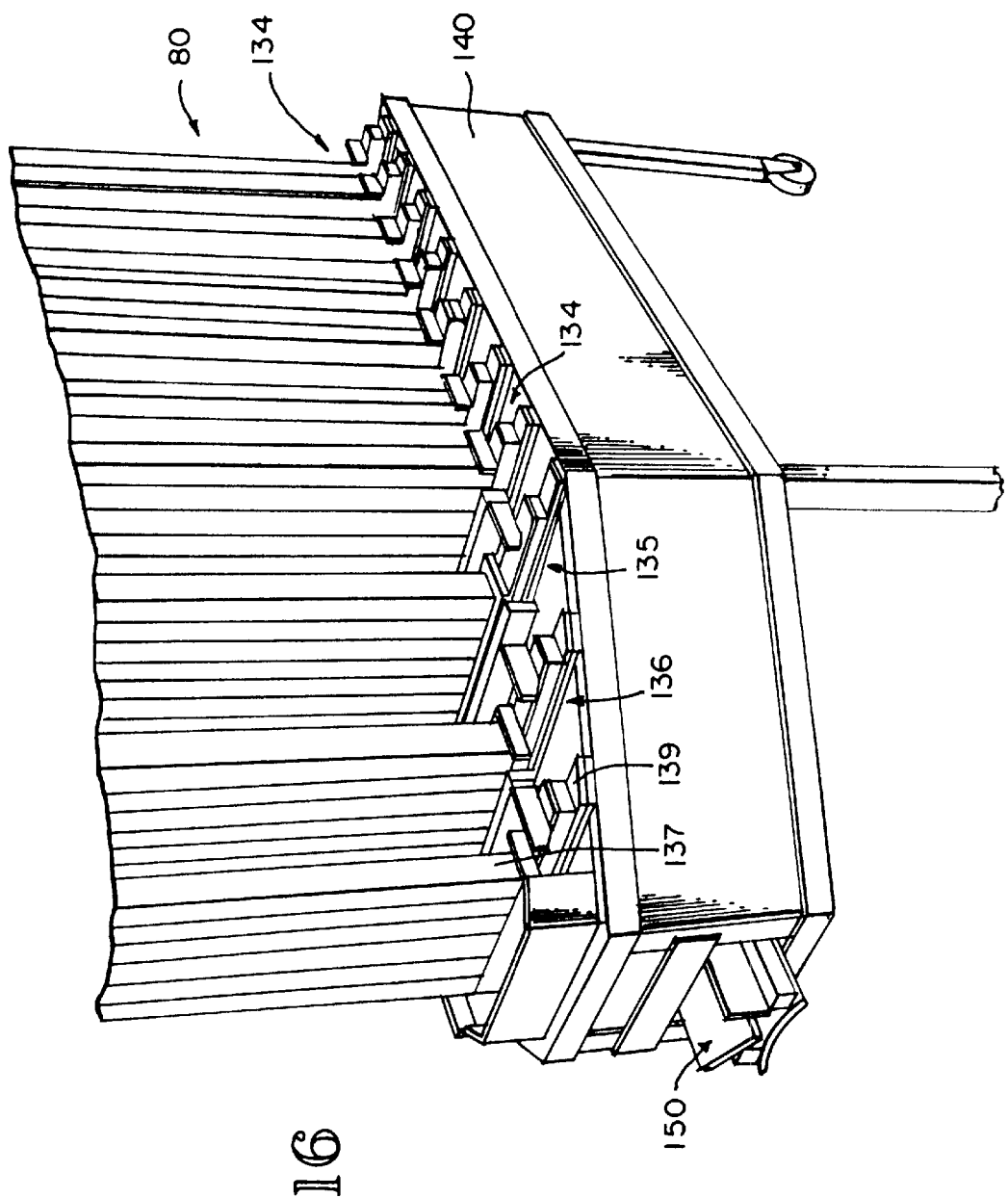
FIG. 16 is a perspective view of one medication vault used in the present invention.

Arranged around collator assembly 78 in the embodiment shown are five substantially identical medication dispensing vaults 80—80 (FIG. 16). In the embodiment shown, each vault includes 104 unit dose storage and ejector assemblies. In a given facility, however, the various vaults could each have a different number of storage and ejector assemblies, to best fit the needs of the particular facility. An ejector assembly (FIG. 17) includes a cartridge holder 137 and an elongated cartridge 138, the lower end of which is positioned within and supported by the cartridge holder and into which are stacked the overjacketed unit doses of a medication. In the embodiment shown, the cartridges 138 are approximately three feet high, although this can certainly be varied, depending upon ceiling height and the volume of doses/supplies desired in a particular cartridge.

Each medication dispensing vault is supported by a vault frame 140 (FIG. 16) set up on wheels in the embodiment shown, which permits each vault to be moved to and away from collator assembly 78, though the system could be made with one or more fixed vault assemblies as well. This permits each vault, as a unit, to be conveniently moved for ready restocking of the individual cartridges as the unit doses are used during the bin-filling process. Also, any number of mobile vaults can be parked nearby for other dispensing purposes, such as "after hours" ten-sector bin narcotics dispensing, medical supplies dispensing or the dispensing of doses for use in a different facility. Due to the large capacity of the system and software monitoring of inventory, the restocking typically will occur at off-hours, such as during the night, although inventory checks are made throughout the day against patient requirements.

The vault assembly shown in FIG. 16 includes a total of 10 banks or rows of storage and ejector assemblies, with seven rows (starting from the rear row) 134—134 having 12 ejector assemblies, the next row 135 having ten ejector assemblies, the next row 136 having six ejector assemblies, and the forwardmost row having four ejector assemblies. The length of the vault assembly could be longer or shorter in a particular case. All of the ejector assemblies are substantially identical, although for large (longer and/or wider) unit dose packages, dual eject members are used. As system requirements change or if a defective ejector is identified, the locations of selected ejector assemblies can be changed easily, due to the portability of the assemblies.

Figure 17:
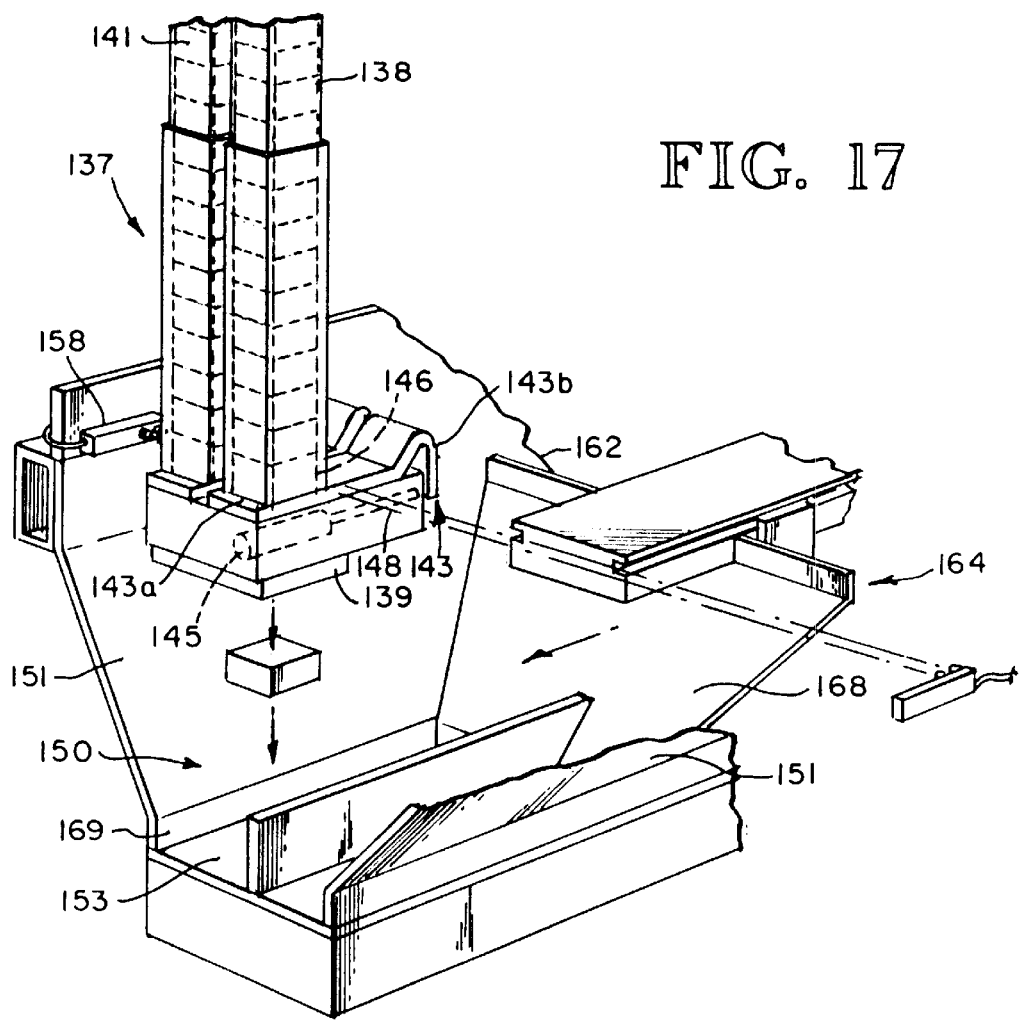
FIG. 17 is a perspective view showing the eject mechanism and associated medical vault trough for one medication vault in the system of the present invention.
Figure 18:
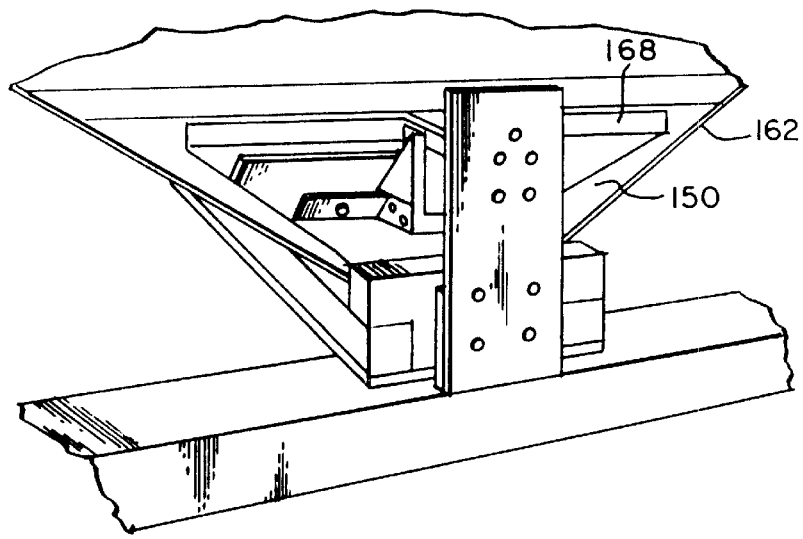
FIG. 18 is a rear view of the assembly of FIG. 17.

Referring to FIGS. 16 and 17, each cartridge holder 137 is a clear plastic element, mounted on a mounting bar 139 which extends the width of the vault. The cartridge holder 137 in the embodiment shown is approximately 9½" high and 2½" square in cross-section. Cartridge 138 fits vertically into cartridge holder 137. Cartridges 138 are made of clear plastic in the embodiment shown, with interior cross-sectional dimensions which are slightly larger than the free-floating overjacketed unit dose packages that they are holding. The cartridges are open at the top and the bottom and also have a vertical opening (approximately finger width) 141 in the front face thereof which extends from nearly the top to nearly the bottom of the cartridge.

An eject member 143 is positioned at the bottom of the cartridge holder. The eject member includes a forward horizontal section 143a, and then angles upwardly and rearwardly and then bends downwardly in a vertical section 143b at the rear thereof, as shown in FIG. 17. The eject member serves a three-fold purpose: to hold the overjacketed packages in place when not in use; to eject a package upon command; and to serve as a stop for doses ejected from the ejector member immediately therebehind.

The eject member 143 is mounted for horizontal movement between rearward and forward positions by means of an air cylinder 145 attached to the vertical section 143b of the eject member. Eject member 143 is held in the forward position (shown in FIG. 17) by air pressure (typically 40 lb.) provided by the air cylinder 145. In its forward position, the horizontal portion 148 of the eject member 143 supports the stacked plurality of overjacketed unit-of-use doses, including the lowermost package 146. Upon a signal from computer 24, the eject member moves rearwardly, sufficiently to permit package 146 to move down to an "eject-ready" position. The front edge of the eject member 143 is adjacent the rear edge of package 146. The rearward movement of the eject member is accomplished by the application of approximately 80 lb. Of air pressure in the rear direction, overcoming the continuous 40 lb. of pressure applied in the forward direction and moving the eject member to the rear.

In the next step, the 80 lb. pressure is removed, such that the eject member moves forwardly, under 40 lb. of pressure, with the forward edge 149 of the eject member 143 contacting the rear edge of the lowermost unit dose package and moving it out of the cartridge holder, as the eject member moves forwardly.

As the unit-of-use dose overjacketed package moves out of the cartridge/cartridge holder, it clears the lateral support bar 139, briefly contacts the rear edge of the eject member in the cartridge assembly located immediately in front of it, and then drops into a vault trough 150. Vault trough 150 is a generally V-shaped assembly which extends across the width of the medication vault and from the back to the front thereof, narrowing toward the front as the width of the vault decreases. Trough 150 has opposed, angled sides 151 with a flat bottom, two-channel surface 153. The unit dose medication package 146 after being ejected from a cartridge unit, falls to the bottom surface of the vault trough.

An LED/sensor combination 158 is positioned in front of each bank of ejector assemblies. When the emitted light is broken by the movement of a unit dose package out of its cartridge, a signal is sent to the robot computer 24, indicating that one dose has been ejected. It is assumed that the dose is the desired one, since the software database links each command to a specific cartridge holder, the identification of which has been scanned and verified along with the bar-code scanning of sleeves at the time of restocking. The same LED/sensor pair is used to monitor the rear of the next forward row of ejector assemblies to confirm proper rearward motion of the ejector assembly in that row. The LED/sensor pair for the first row will monitor only ejection of packages in that row, while the LED/sensor pair at the rear end of the vault will monitor only rearward motion of the ejector assemblies.

When a unit dose package is to be ejected, the larger rearwardly directed air pressure is briefly applied, causing the eject member to move rearwardly, as discussed above. If the eject member does not move to its rearmost position during such activation and break the LED/sensor beam, that signals a fault in the system at the operator's station monitor. When the eject member is in its rearward position and the next package has dropped into place, the higher air pressure is turned off, as indicated above, allowing the lower, constant pressure to move the eject member back to its forward position. This forward action moves the dose out of the cartridge which breaks the light beam of the LED/sensor, and indicates that the dose has been ejected.

It should be noted that only one eject assembly on a given bank is "fired" at a time. The sequence is in fact, however, very close in time. The sensors wait for only a 3–5 milliseconds interval to pass before a second ejector assembly is fired in the same bank. This appears to the human eye as essentially simultaneous. It should be understood that two or more desired medications for a particular bin may be stored in the same vault and therefore such near simultaneous firings do often occur.

All of the medications for a particular patient's bin are ejected within a very short time, typically under 100 milliseconds, regardless of the medication vault(s) in which the desired medications are located. The robot computer knows the exact location of the particular cartridge for each medication stored in the vaults and provides the necessary signal to the eject member (in particular, the air cylinder valve) associated with the correct cartridge in order to eject the desired medication dosage packages into their associated vault troughs.

For a hospital patient's three-sector bin, the medications ejected will include in respective sectors all of the medications for the next imminent dosage time, any medications specified "as needed" and off-time specialty medications. The software can, as explained above, assign sectors in the bin for particular dosages. For example, if a doctor ordered numerous "as needed" doses and few off-time doses, the software can designate the large 144° sector as the "as-needed" sector, to avoid crowding/overflow problems.

With respect to each sector's medications, for the next dosage time, all of those medications, in their packages, will be lying in the various vault troughs after the ejections from their respective cartridges.

Normally positioned at the outboard end 162 of each vault trough is a plough assembly 164. Plough assembly 164 includes a pusher plate 168 which is shaped to conform to the configuration of the vault trough. Plough assembly 164 also includes a pressurized air cylinder, which when actuated moves plate 168 along the vault trough to the inboard (mouth) end 169 of the vault trough. As this occurs, any medication packages which have been ejected into the vault trough are swept along in front of the plough. Sensors are arranged on the air cylinder to sense the position of the plough at the forward and rear ends of the trough.

Figure 14:
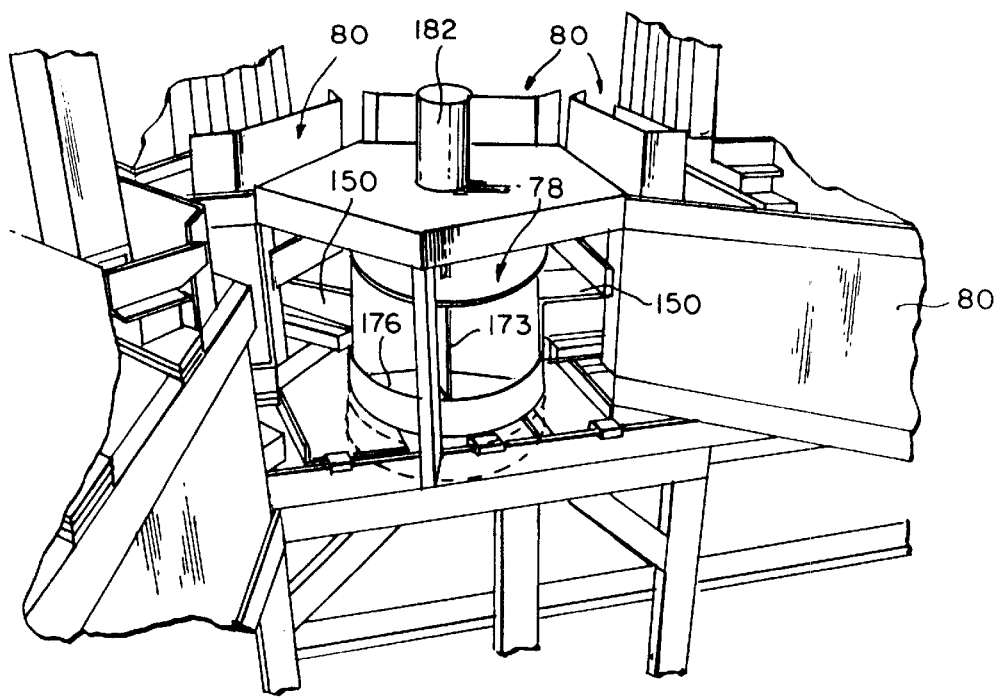
FIG. 14 is a perspective view showing the central collator portion of the system of the present invention.
Figure 15:
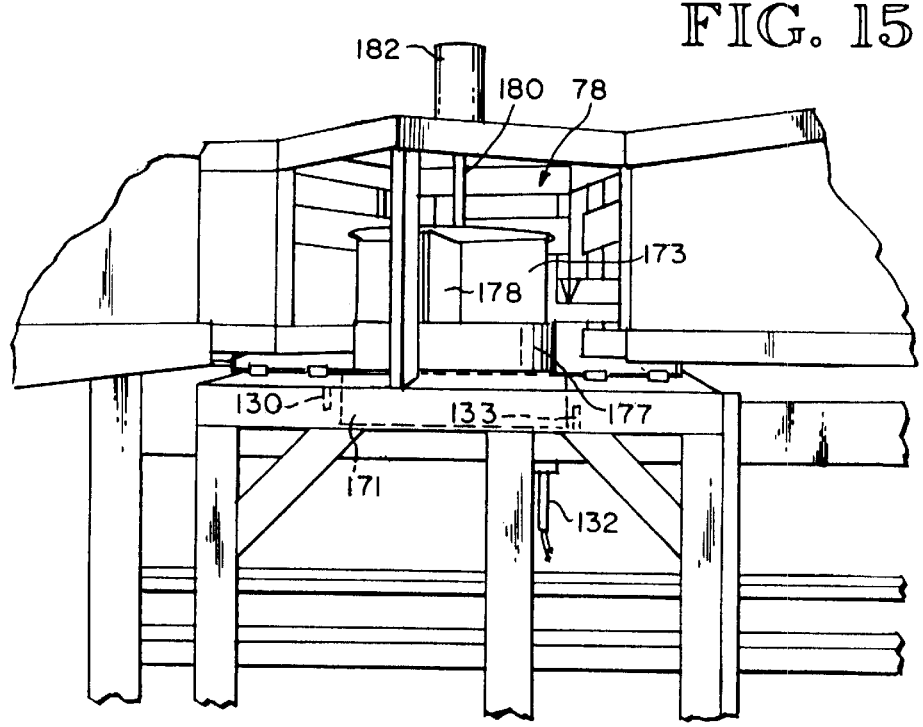
FIG. 15 is an elevational view showing the central collator of FIG. 14.

At the far end of its stroke, plough assembly 164 moves the medications into central collator 78. As can be seen in FIGS. 14 and 15, the central collator 78 is circular, divided into five 72° sectors by means of thin, spaced, fixed vertical plates 173—173 (approximately 9" high) which extend from a vertical center element of the collator to the periphery thereof. The periphery has a short wall 177 (approximately 3" high) which is connected to the outboard edges of the vertical plates 173. The collator has approximately the same diameter as the patient bins, shown in dotted lines 171 in FIGS. 14, 15. Collator 78 is open at the top, with a pneumatically actuated bottom sliding trap door 176, which may be opened at desired times. The plates 173, the wall 177 and the trap door 176 define successive sectors around the periphery of the collator, for temporarily containing medication from the vaults, above the proper sectors of bins as the bins arrive beneath the trap door 176.

Each of the fixed dividing plates 173 has a movable plate 178 immediately adjacent thereto when the collator is to feed a five sector patient bin. The movable plates 178 can be rotated laterally to a point approximately halfway to the next adjacent fixed plate, at which point it is fitted into a small slot at the periphery of the sliding door. This action converts a five-sector collator into a ten-sector collator for use with ten sector bins, such as the drug-specific bins referred to generally above. The collator 78 is mounted on a vertical shaft 180, at the top of which is a stepper motor 182 which, in operation, rotates a small distance away from its "home" position in order to collect doses which have been ejected and swept to the collator from a particular vault before returning to its home position in time for the actuation of the trap door. The action of the collator 78 is accomplished in controlled fashion, by means of signals from robot computer 24.

In a typical operation, the doses are strategically located in particular vaults such that the required doses for a particular patient will fall into the correct channel and be swept therealong until they reach the collator, without having to rotate the collator. However, this three-step fill process (dose eject, plough sweep, trap door actuation) will not work as indicated above if a needed dose for a particular bin sector is stored in a vault opposite the particular bin sector into which that dose is to be delivered. When this situation occurs, the trap door remains closed after a first plough operation and the collator then moves (spins) so that the correct sector of the bin is aligned with the correct vault to receive the additional dose. The collator then spins back to its home position and the trap door is released.

If necessary, these actions are repeated for all the vaults until all the required medication doses have been swept into the proper sectors of the collator and from there into the bin therebeneath. To fill five-sector bins and ten-sector bins, the procedure discussed above is identical, with the collator being rotated to accept the medications desired for each collator sector in turn.

When all the desired medications are present in the collator, which occurs very rapidly, typically within a few milliseconds for a standard three-sector bin, the collator is rotated back to its home position where its own sectors are always in registry with the corresponding sectors in the patient's bin located directly beneath. The sliding trap door 176 is then actuated by the control computer 24 to move horizontally beneath the collator by an air cylinder or similar mechanism. The medications in the collator 78 then fall into the corresponding sectors in the patient bin 171. The patient's bin 171 is now filled. The sliding trap door 176 is then moved back (closed) to its original position.

The patient bin 171 is now ready to be moved away from the central collator, by an outfeed shuttle assembly 82. The outfeed shuttle assembly 82 is shown generally in FIGS. 19–21. Just prior to the bin being filled, a bin retriever assembly 184 moves beneath the central collator 78 and the filled bin. The retriever assembly 184 includes a bin latch mechanism 186. The bin latch mechanism includes two vertically oriented plates positioned adjacent each other, with one plate 187 being rotatably connected to the other at a pivot point 189 near a rear end thereof, i.e. the end toward the central collator 78. Plate 187 includes a cutout section 192. As bin latch 186 reaches the central collator 78, a pin 194 extending from plate 187 moves past a cam on the shuttle assembly frame, the cam forcing plate 187 upwardly and locking it in place at an angled position above a ball detent 191 in the surface of plate 187.

Figure 22:
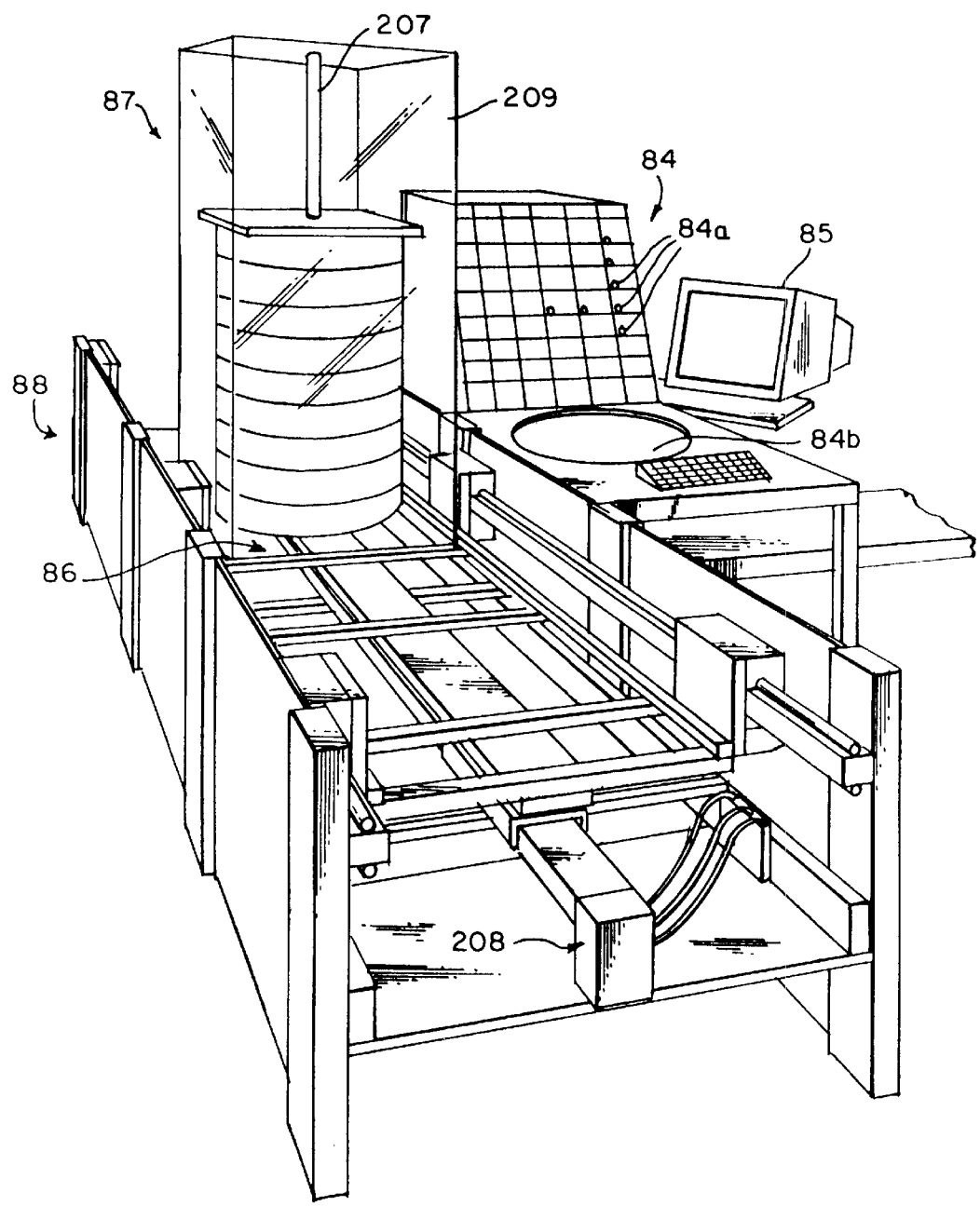
FIG. 22 is a perspective view showing the outfeed portion of the system of the present invention.

In this position, an extending edge 198 of plate 187 hooks against the lower edge of the bin. The retriever assembly 184 is actuated by an air cylinder 200, which moves the bin along two spaced tracks similar to the infeed shuttle tracks. The filled bin is moved along the spaced tracks by the retriever assembly to its next position, which is a mobile SD (supplemental dose) cart 84, where an operator is stationed (FIG. 22). It is at the SD cart 84, where the operator supplies the "slow mover" medications which may be prescribed for a particular patient, but which are not located in the medication vaults.

The SD cart 84 includes several horizontal rows of bar coded bins, the rows spaced one above the other in a tiered fashion, for ease of access, with a selected number of bins in each row. A typical SD cart will have 7–10 rows, each row having 6–10 bins. Each of the bins has an LED light (partially shown in FIG. 22) 84a associated therewith. Prior to actually beginning a fill cycle for the hospital or other facility, the robot computer is aware of the "slow mover" medications which must be provided in the various SD cart bins for that particular full cycle.

As discussed briefly above, the slow mover medications (approximately 1500–2000) are arranged in storage around the periphery of the room housing the robotic bin-filling system. Prior to each fill cycle, an operator will disconnect the mobile SD cart, move it to the surrounding storage (usually on shelves) and with the aid of a menu-driven RF hand-held scanner (not shown), will locate and scan the "slow mover" medications for the next run, information provided by the hospital computer 20.

The operator will pick the scanner-displayed medications from storage and will place them in specific bar-coded SD bins by a menu-driven scan verification process. The operator will scan the bar code on the particular storage location of the slow mover medication, as well as the bar codes on the overjacketed package itself and the particular SD cart bin in which the slow mover medication is to be temporarily stored. The computer thus knows the precise SD cart bin location for each slow mover medication to be dispensed in the next cycle. When all the slow mover medication doses have been collected, the operator will roll the SD cart back into position at the operator's station, downstream from collator 78.

As each bin which has been scanned at entry is moved to the central collator and then filled, those patient bins which are to have "slow mover" medications therein are stopped briefly at the SD cart station to receive one or more slow mover medication doses. A signal has been previously transmitted by the robot computer 24 to the appropriate bin(s) on the SD cart, lighting the LED(s) 84a associated therewith, before the particular bin is grabbed by the infeed shuttle system, thus alerting the operator to the correct SD bin(s) in which the slow mover doses for the particular patient bin which will be in front of him next is located.

Prior to the arrival of a patient bin needing one or more slow mover doses at the SD cart, the operator scans the bar code(s) on those SD bins having blinking LED lights, reaches into the bin(s), grabs and scans the unit-of-dose therein. The operator then waits for the patient bin to arrive at the SD cart and observes the touch screen monitor 85 which shows the proper sectors in the patient's bin for the doses picked. When the patient bin arrives and stops at the SD cart, the operator drops the doses into the correct sectors of the bin through opening 84b in the cart and confirms the exact placement by touching the destination sector on the computer monitor, which in turn reactivates the retriever assembly to move the bin to the upload elevator 86.

The upload elevator 86 operates in conjunction with the outfeed cassette conveyor 88, as shown in FIG. 22. The outfeed cassette conveyor 88 is similar to the infeed cassette conveyor 72. The cassettes are moved along by a stepper motor and lead screw arrangement 208 similar to that for the infeed cassette conveyor. An empty cassette (not shown) moves into position over the upload on elevator 86, with a latching pole assembly 207 extending downwardly through the center of the cassette housing. The upload elevator 86, similar to download elevator 74, is movable vertically and has an opening in the center thereof through which the cassette latching pole assembly extends.

A filled patient bin is moved onto the upload elevator by the retriever assembly (FIGS. 19–21). As the bin moves into position, the bin latching mechanism underneath the bin on the retriever assembly comes into contact with a cam element on the frame of the outfeed shuttle assembly which releases plate 187 of bin latch mechanism 186, so that it moves downwardly past the ball detent. Plate 187 releases the bin it is holding, and is held in a lower position by the ball detent, so as to maintain it out of contact with the bin. The retriever assembly 184 is then returned to the center collator to pick up the next bin.

The filled patient bin just released by the bin retriever assembly is centered on the upload elevator plate, which is then moved upwardly, thereby moving the bin past the extending spring-biased ears of the latching pole assembly. The ears move inwardly as the bin moves up the pole. As the bin clears the ears, the ears spring outwardly, supporting that bin on the pole. The elevator plate is then lowered to receive the next bin. Each successive bin is loaded onto the latching pole in similar fashion until ten bins (or other pre-established number) are loaded, completing the cassette. The outfeed conveyor then moves the completed cassette away from the upload elevator, while positioning the next pole and latching mechanism at the top of the upload elevator for building the next cassette, the bins for the next cassette comprising those which have been disassembled from a cassette at the download elevator and now moved through the system.

It should be noted that in the overall bin-filling process the individual patient bins are unloaded from a cassette on the infeed conveyor and accumulated on a cassette on the outfeed conveyor in reverse order, i.e. the patient bin at the bottom of a full cassette on the infeed conveyor is positioned at the top of the corresponding cassette on the outfeed conveyor. The robot computer takes this into account automatically. Each bin's precise location in the cassette is precisely tracked and the location thereof is thus known at all times, both during the bin-filling process and as cassettes are positioned in transfer carts, medication carts (on the ward) and vending cabinets (on the ward).

While the individual patient bins are actually filled one at a time, it should be understood that the overall process is both continuous and overlapping, i.e. while the patient bins do move serially through the filling process, there are bins at various points within the system at any one time, thereby providing a multiple processing capability. For instance, as one patient bin is being uploaded into a cassette on the outfeed conveyor, successive bins will be at the SD cart station, at the central collator, and on the infeed shuttle, while simultaneously, doses from any or all of the vaults are being ejected and ploughed, while the collator is spinning into its proper position.

Further, the true parallel nature of the medication vault dispensing system should be understood. The desired medications in a particular sector of the patient bin being filled are ejected in rapid succession, virtually simultaneously, in each vault, with each vault operating independently, but simultaneously with all other vaults, until all the medications for all sectors of the patient bin are in the various vault troughs.

All five vault ploughs are virtually simultaneously activated to drive all doses substantially simultaneously into their respective sector positions above the trap door, precisely aligned with the patient bin in position below the trap door. In a circumstance where an additional dose may be needed from a particular vault not already aligned with the correct bin sector, the five-vane collator is rotated rapidly away from its home position to properly line up with the correct vault, which may have already ejected the dose units into its trough in preparation for the plough moving the dose into the collator.

It should be understood that the hundreds of different dose types (medications) are positioned in the various vaults in the most efficient locations possible, with a goal being to avoid rotation of the central collator 78 whenever possible. Thus, the collator 78 will usually spin through an angle sufficient to collect one or perhaps two doses before quickly returning to its home position. Often, the collator will not have to rotate (spin) at all to completely fill a patient bin.

After all required doses are ploughed into the proper collator sectors and the collator is in its home position and the patient bin is in position below the collator, the trap door is opened and the doses drop into the proper sectors in the bin. The filled patient bin is then captured and moved by the outfeed shuttle system. Hence, the bin-filling process has both multiple and parallel processing aspects, adding to the speed of the overall process.

The multi-tasking, parallel bin-filling process can therefore be quite fast, i.e. from the time that the bin is removed from its cassette on the infeed conveyor to the time that it is loaded into a corresponding cassette on the outfeed conveyor can take as little as several hundred milliseconds, with a theoretical maximum time of 1.7 seconds per bin. All of the patient bins in an average hospital of 200 beds should theoretically be filled within 15 to 20 minutes or less, depending upon the particular number of patients being serviced. This is a very significant improvement in time over any current system, perhaps hundreds of times faster than the fastest existing hand-implemented, automatic or semi-automatic systems.

Further, because of bar-code control, the accuracy of the bin filling process relative to a particular patient's bin receiving current, up-to-the-second correct medications in the right sector is very high and can approach a near zero error rate, which is significantly better than existing manual systems and semi-automatic systems, which by comparison will typically have over 100 times more errors.

Figure 23:
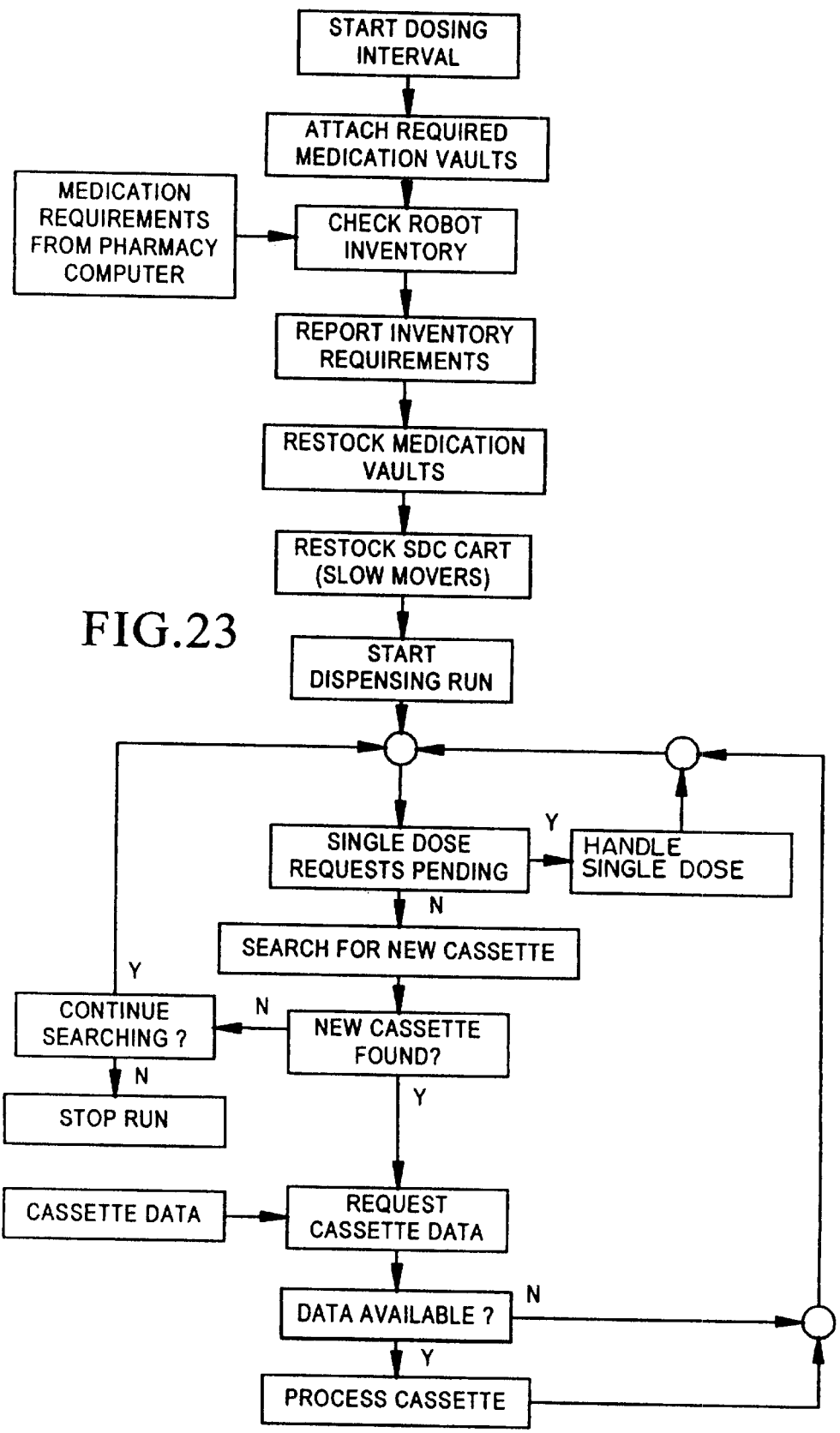
FIGS. 23 and 24 are software flowcharts for the system of the present invention.

FIG. 23 is a flowchart summary of the successive functional steps for the stocking sequence and also a single medical element-dispensing run for a given facility, such as a hospital. Each of the individual steps has been discussed in detail above, and hence will not be repeated here.

Figure 24:
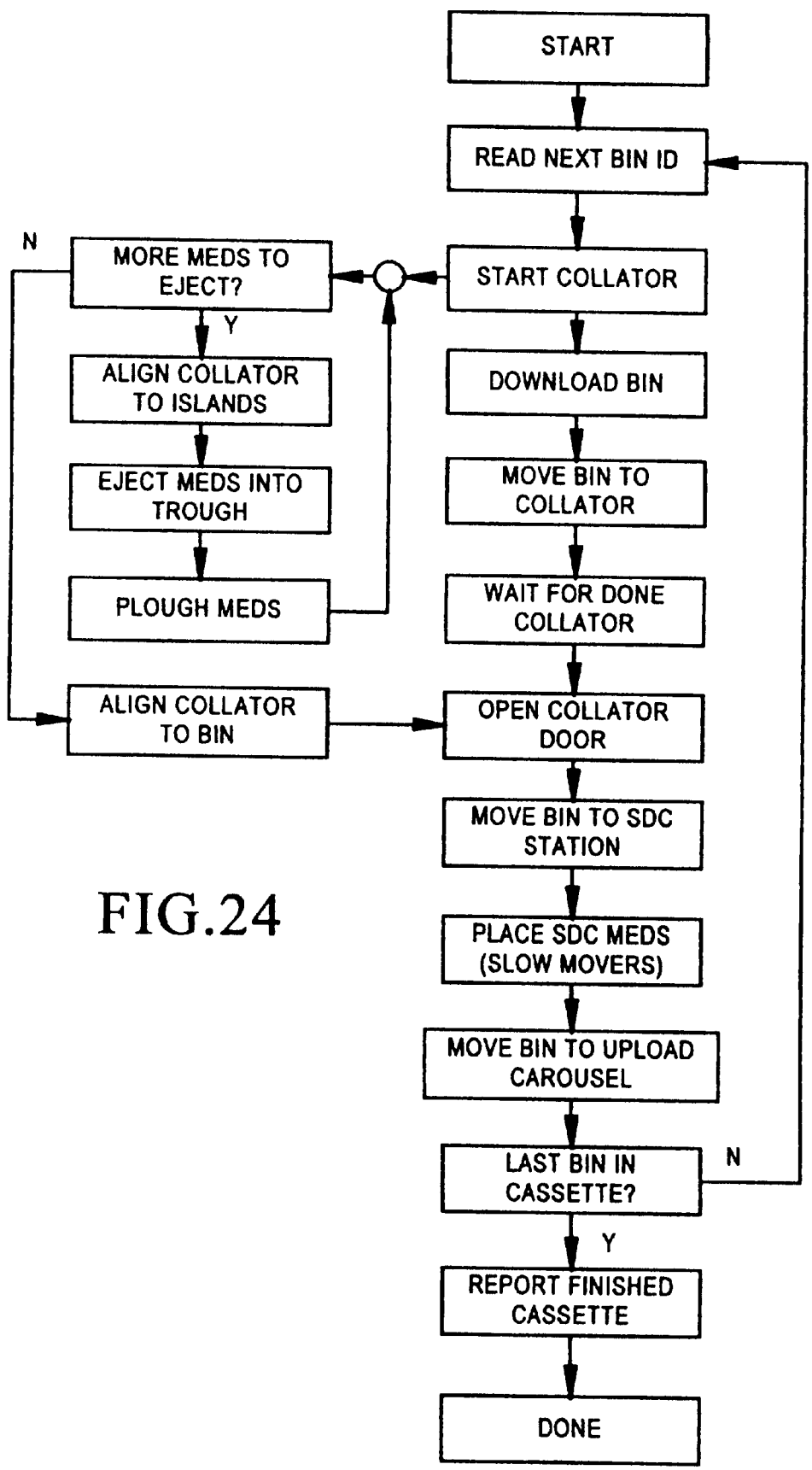

FIG. 24 is a flowchart summary for the filling of the bin receptacles in one cassette. Like FIG. 23, the flowchart of FIG. 24 sets forth a series of steps, each of which has been described in detail above. These flowcharts can be used by a programmer to produce the actual software code which results in the individual functional steps.

Figure 25:
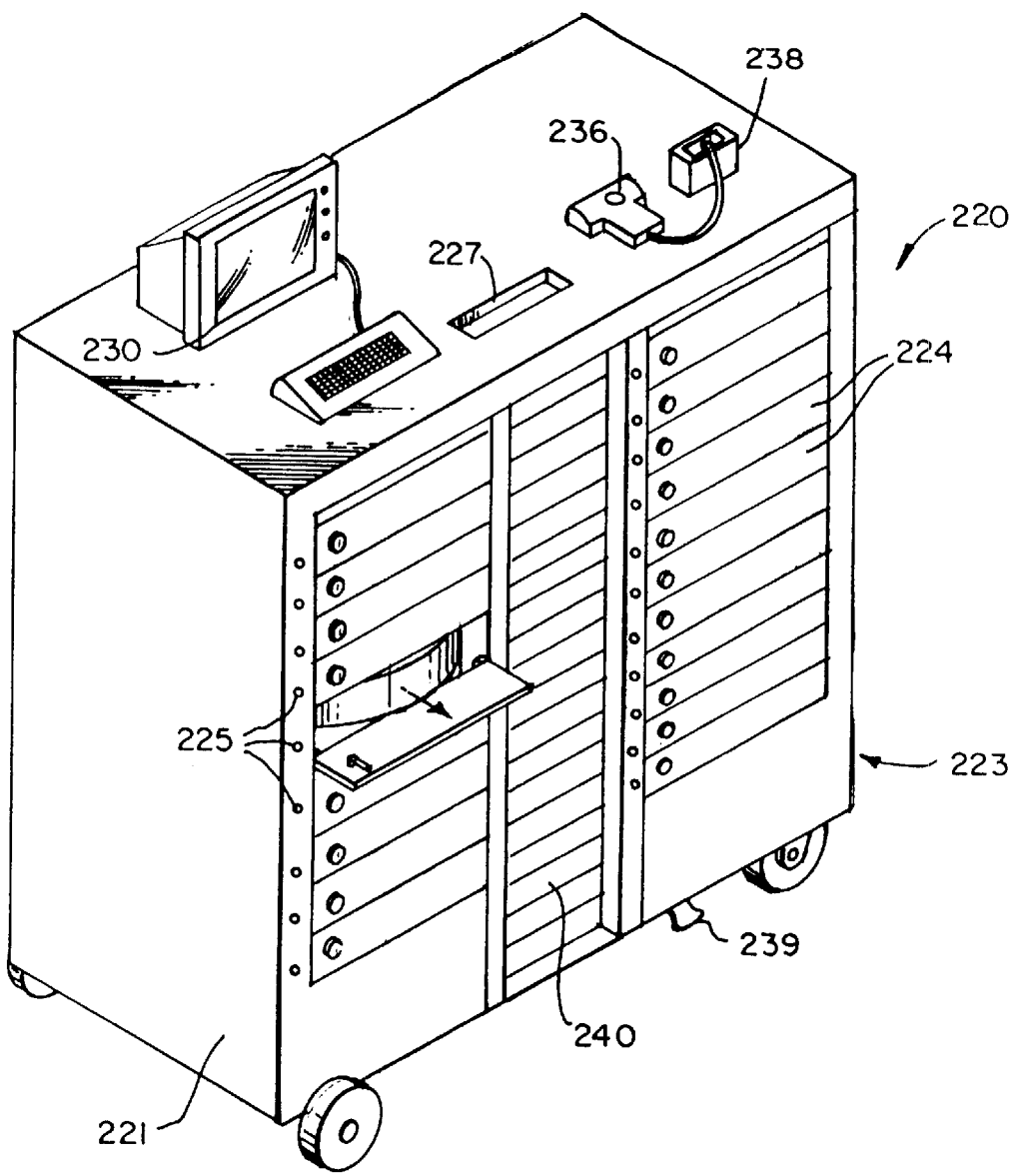
FIG. 25 is a perspective view of a medication cart for use in the system of the present invention.

Once the cassettes are filled, they are then loaded onto a transfer cart and moved by a courier to the various wards or other patient care areas. At the ward, a transfer of the cassette is made from the transfer cart to either a mobile medication cart or stationary vending cart. The mobile medication cart is shown in FIG. 25. The medication cart, shown generally at 220, includes a frame 221 which houses three cassettes in the embodiment shown, typically two ten-bin patient cassettes and one 20–24-bin drug-specific cassette. Each of the cassettes is mounted on an electronically encoded Lazy Susan platform. Transfer access to the interior of the cart (and the cassettes) is through a locked door, usually at the rear of the cart.

The Lazy Susan is physically indexed relative to the cassettes such that a cassette can only be placed on it in one particular physical orientation. This becomes the "home" position of the cassette. A sensor/encoder monitors the rotational movement of the Lazy Susan so that the rotational orientation of the bins is always known by the cart on-board computer and via an RF link, the nursing station computer 37 as well.

When the cassettes are loaded on the Lazy Susan, the individual bins in the cassettes are accessible from one side 223 of the medication cart. Aligned vertically with each cassette are a series of flip-down bin doors 224, with each door being positioned so as to prevent/permit access to a particular bin in a cassette.

Access to a selected single bin and more particularly to a single sector of a bin is provided by operation of the bin flip-down door on the cart associated with the selected bin. The bin access doors may take a variety of configurations, but in the embodiment shown, the access door comprises one flip-down door associated with each bin, so that the individual bins are not visible from the front of the cart, and none of the sectors of the bins can be removed, nor can access to any of the sectors be gained, due to the effective blocking by the access doors. The doors can be interconnected to form a panel of doors, which can then be removed and replaced as a unit.

The Lazy Susan includes a brake mechanism (not shown), so that when a Lazy Susan and the cassette thereon is rotated, the Lazy Susan and the cassette can be stopped at the precise rotational position which makes accessible the sector of the particular bin from which the desired medication is to be taken.

Access to the bins is as follows. The medication nurse gains access to the wall-locked medication cart by scanning his/her ID badge bar code and then entering a PIN (personal identification number), which results in the cart being released from the wall. The nurse will then roll the cart from bed to bed or patient to patient. When a patient is to be provided medication from his/her individual bin which is present on the medication cart, the bar code on the wristband of the patient is first scanned by the nurse, using a bar code scanner 236 present on the cart. This results in a signal to an RF radio controller (not shown) which communicates with the hospital information database to obtain the latest medication orders.

The RF controller then transmits an RF command signal to the medication cart computer (not shown), which actuates a blinking light 225 adjacent the patient's bin, displays the patient's name on an LCD display 230 at the top of the cart, and activates the Lazy Susan spin motor to position the correct sector of the patient bin adjacent the flip-down door. When the nurse returns to the cart and places the scanner into its cradle 238 on top of the cart, the correct door flips open, exposing the desired sector of the specific patient bin which contains the proper doses for the patient.

In another approach, the cassette may be manually rotated (spun) by the nurse and the cassette then automatically stopped at a correct orientation under control of the cart's computer, such that the desired sector only of the bin is presented to the nurse, without use of a spin motor for the Lazy Susan. The bar code on the bin can be scanned to ensure a correct match between the bin and the patient as a redundant check for proper operation of the Lazy Susan apparatus.

The nurse then slides the accessible sector of the patient bin outward, removes the bar-coded overjacketed packages to the top of the cart, and scans the package bar codes to ensure that they are correct and up-to-date. These steps ensure accuracy and eliminate errors. If the medication is correct, as verified by the nursing station computer with a particular audible sound, the nurse gives the medications to the patient. If the medications are not correct or are out-of-date, according to the nursing station computer, a different audible sound directs the nursers attention to the display 230 for further instructions, such as dose discontinued, with further instructions to drop the medications into slot 227 on cart 220. If any doses are missing, the nurse can order a replacement with a keystroke, thus eliminating time-consuming troubleshooting phone calls.

The scanning of the bar codes (or other identifying information) on the patient, the nurse and the medications may be accomplished by a portable, hand-held bar code scanner 236, which may be placed in a scanner receptacle (cradle) 238 in the top surface of the medication cart, to allow hands-free operation by means of a foot pedal 239 or cart top scan activation device (not shown). The use of a hands-free scanning device on a mobile medication cart can have many operational advantages, among them speed and reliability. In operation, the scanner is briefly activated until the bar code scan is completed and then automatically turned off, in order to conserve power. The nurse passes each bar code medication or supply in front of the scanning light until all have been processed. After the medication is given by the nurse to the patient, the particular sector is moved (slid) back to its original position in the bin, and the bin door is closed and locked.

The closed and locked condition of the cart doors is sensed by the on-board cart computer. When this is accomplished for all of the patients having bins in the cassettes on board the medication cart, the nurse will then roll the cart back to the docking station cabinet to relock the cart into its stationary position near the nurse's station. This movement of the cart is typically done four times per day for the four normal dose times. Doses which may be required between those times or before the next cassette will typically be in the other sectors of the patient's bin in the mobile cart. Usually, the nurse will obtain the additional doses directly from the "docked" cart using the steps described above. Once those off-hours doses are obtained, the nurse will carry the scanner and the doses to the patient to administer the dose and record the action.

Later, just prior to the next usual dose time, a courier will move a transfer cart to the ward with new filled cassettes for all the patients, for exchange with the empty (or near empty) cassettes used for the previous dose time and the intervening time. Each patient thus has two bins in the system, one on the mobile medication cart at the nursing station and the other either en route to or from the nursing station or in the robot-dispensing facility.

The third cassette 240 in the medication cart, usually positioned in the middle of the cart, is usually a drug-specific cassette, access to which is provided when certain medications are to be administered which are not in the standard patient bins such as certain narcotics, starter doses, after hours doses, etc.

As indicated above, the use of bins associated with a patient with bar coded information and the use of frequent scanning permits very accurate control over the filling and dispensing of medications to a particular patient. The system forms a "closed loop" with the hospital information system, tracing the use of all medications and medical supplies within the institution, virtually error-free. This is a tremendous advantage over existing systems, which are typically independent of the hospital information system in one way or another.

It also helps with "just in time" (JIT) medication dispensing, so that the only medications in a patient's JIT dosage sector will be the specific medications due at the particular major dose time, i.e. 8 AM., 12 Noon, 4 PM. or 8 PM. The medication cart will typically arrive in the ward just before those four major dose times, with the "due now" medications in the one JIT sector being for that particular dosage time. PRN doses will be in the PRN sectors and any interval doses will be in the third sector.

Figure 26:
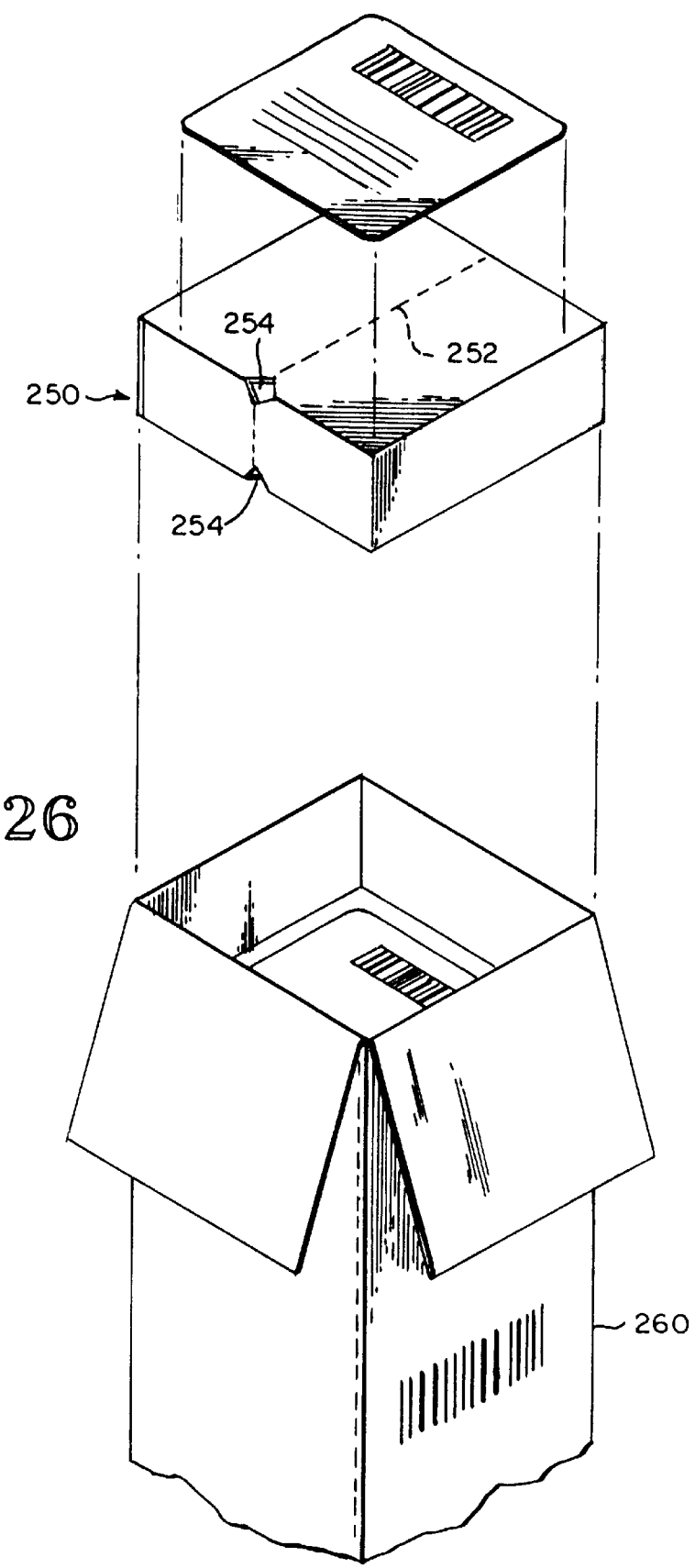
FIG. 26 is an exploded view showing the overjacket packaging for the medical elements used in the system of the present invention.

As indicated above, one of the key aspects of the present system is the use of a particular "overpackaging" regimen. Referring to FIG. 26, typical unit-of-use doses from the drug manufacturers or other medical supplies are first individually put into uniform overpackages, also referred to as overjackets. In some cases, the unit doses or other supplies will come in their own packages. These packages are also placed in the overpackages described herein. There are five or perhaps more specific sizes of overpackages, each with a bar code identifying the unit-of-use dose or medical supply contained therein. FIG. 26 shows a typical overpackage 250. The overpackage 250 is typically made from paper and includes a line of perforations 252 around a substantial portion or all of the package shown in FIG. 26 at about mid-length thereof, although some perforation lines may be placed off-center on some overjackets. Larger openings 254 may be provided at each end of the line of perforations, which make it even easier for the overpackage to be opened, exposing the unit-of-use dose or supply therein.

The individual overpackages 250 are positioned in a disposable paper sleeve 260 which is capable of receiving a selected number of the individual overpackages. The sleeves (with the overpackages therein) are arranged to readily fit within the cartridges on the robot-dispensing medication vaults, and are provided to the individual robot facilities by overnight delivery from the national facility. During off-hours, such as at night, the individual cartridges in the medication vaults are filled by inserting the filled sleeves therein and then removing the sleeves, leaving the overpackages in the cartridge. The sleeve packaging is thus a convenient way of transporting a plurality of unit-of-use overpackages and loading them into the robot cartridges.

Besides individual medication dose units provided to the nursing stations in patient bins, the present invention also contemplates various types of bin "kits" in which, for instance, single, double or triple ten-part bins may be prefilled with specific items for a particular hospital function. These could include, as examples, emergency kits (typically a pair of bins), surgical kits in which each bin would contain various surgical pharmaceuticals, implements and/or supplies, or anesthesiologist kits containing anesthesiology pharmaceuticals, implements, and/or supplies. The bins will be contained in a short "kit" cassette, with at least one such cassette being placed in a mini-cabinet in the applicable location, such as in an operating room, in the middle of a shared suite of operating rooms, an intensive care unit, an emergency room or other medical specialty area.

Hence, while the primary use of this invention will be to contain medications and supplies for individual patients, the principles of the invention can be used to compile special purpose kits which then can be conveniently located in specialized areas of a hospital, clinic, emergency care facility, nursing home or other similar health care facility, with the cassettes being exchanged once per day to replenish the used bins.

Besides the above-described medication carts, specialized medication cabinets are possible with the present invention. For instance, micro-cabinets, such as at a particular nursing station, containing a pair of ten-part bins with manual access, can contain emergency medications which are normally used in life-threatening situations. These micro-cabinets can also be replenished on a regular basis, using the robot-dispensing apparatus, i.e. daily if necessary, or at other convenient intervals. Drug-dispensing cabinets containing one or more cassettes, each containing a plurality of ten-part drug-specific bins can be used in a hospital emergency room, an out-patient clinic, outside emergency care facility or other health facility.

A similar cabinet can also be used as a "docking station", in combination with the medication cart described above. The docking cabinet is designed to periodically link up with the medication cart and provide a recharging capability for the medication cart. Also, such a docking cabinet would itself contain a cassette of drug-specific bins on an electronically controlled Lazy Susan. The docking cabinet would typically be present at the nurse's stations in hospital or nursing home patient wards.

The above-described system, besides providing accurate control over the dispensing of medications and other supplies, also provides a capability for accurate and up-to-the-minute, complete inventory control for the facility, so that items are ordered only as needed and are not over-stocked or understocked. Every item is accounted for, virtually error-free. Accurate stocking quantities can be ascertained based on actual use of the medication over a period of time.

In summary, the system of the present invention is an automated arrangement which includes obtaining unit-of-use dose medications and other supplies directly from manufacturers, packaging them in specific size bar-coded containers or carriers of substantially rigid material such as cardboard, referred to as overpackages, which are subsequently inserted into bar-coded sleeves and then transported to facilities which contain a robot medication-dispensing assembly. Up-to-date usage information results in accurate re-ordering of medications and supplies. The individual bins to be filled by the robot assembly can be related to a specific patient, in response to up-to-the-minute orders by a physician. The patient's physician will provide orders to the central pharmacy in the hospital or other facility through the facility information system module referred to as "order entry". These orders are checked by a trained pharmacist for any drug therapy questions. After the order has been processed and approved by the pharmacist, it is entered in the robotic computer which controls the filling of the specific bins.

As described above, the bins are individually filled by the robot dispensing assembly from stacks of bins referred to as cassettes which are placed on an infeed conveyor and removed on an outfeed conveyor. The filling of the bins takes place very quickly and very accurately for an entire hospital, nursing home or other facility. The filled cassettes are manually loaded onto a transport vehicle known as a transfer cart and moved to the patient care areas for full-for-empty cassette exchanges to/from the medication carts/cabinets at the nursing station.

The medications are dispensed to the patient from a locked medication cart, access being provided to one desired bin therein by means of a bar code scanning device and an RF signal from a portable scanner to the medication cart computer which controls on-board devices which provide access to a desired bin when activated. Bar codes are used to maintain control over the medications and to ensure that the correct patient receives the correct dose units of the prescribed medications at the right time. The individual bins containing the medications may be three-sector bins, which are typically used in a hospital setting, or they may be five-sector bins, which are typically used in other medical facilities, such as nursing homes, or the bins may have other numbers of sectors, depending upon the particular situation and purpose, either patient-specific or drug-specific.

A central facility containing the robot dispensing assembly, located either at a large hospital or some other multi-facility centralized location, can transfer filled bins in cassettes via trucks or other transportation modes to smaller facilities, on a daily, weekly or other regular basis. Thus, a variety of facilities, small hospitals, clinics, nursing homes of all sizes, and other medical facilities, can utilize a central robot assembly facility via conventional transportation modes. It is also possible, for instance, for an outpatient doctor's office to have a medication cabinet which is serviced on a regular basis with medication cassettes containing pre-counted outpatient prescription containers.

When the doctor in his office prescribes medication for a particular patient, such as at an office visit, the medication cabinet will have the capability of printing the required label with the correct dosage information, and the prescription can be filled from the cabinet. In those states which may require a pharmacist's review prior to the issuance of a new prescription, the pharmacist could counsel patients at the clinic or remotely by video conferencing or the like. The patient can thus receive the prescribed medication right at the doctor's office instead of having to go to a pharmacy.

The individual bins can be in the form of drug-specific bins, in which the bins contain certain specific drug dosage units, such as narcotics or emergency room drugs. Special bin "kits" can be produced which meet special needs, such as in surgery or anesthesiology. This can all be done with the robot dispensing assembly in combination with the supplemental dose (slow mover) cart which is manned by an operator.

The above-described system has significant potential advantages over current systems. It is completely automated, thereby providing a high degree of accuracy, as well as inventory control. It is substantially faster than any existing system and eliminates a substantial amount of hand-labor on the part of trained pharmacists, enabling them to utilize their skills and knowledge for drug therapy as opposed to filling pharmaceutical orders. The system will also substantially reduce medication handling labor during the medication administration process. The present system can provide patient medications "just-in-time" for the current dose event, incorporating any up-to-the-minute change in medication orders, as well as preventing errors or confusion by having just the current medication dose available.

The use of bar codes throughout the system provides a significant amount of information and control over all aspects of the system, including the dispensing of correct medications to the correct patient bin in a reliable and timely manner.

Although a preferred embodiment of the invention has been disclosed herein for illustration, it should be understood that various changes, modifications and substitutions may be incorporated in such embodiment without departing from the spirit of the invention, which is defined by the claims as follows:

What is claimed is:

1. A portable medication cart for dispensing medical elements, including medications, to patients in a healthcare facility, comprising:

a portable medical elements cart;

means within the cart for storing medical elements; and a holder member located on a surface of the cart readily accessible by an operator for holding a scanning device used for identifying medical elements, such that an operator can scan a particular medical element without holding the scanner wherein the holder member is located remotely from a storing means for the medical elements and is not part of a dispensing system for the medical elements from the storing means, wherein the medical elements to be scanned must be removed by the operator from the storing means prior to being scanned by the scanning device.

2. An apparatus of claim 1, including a plurality of rotatable support means, each rotatable support means supporting a stack of a plurality of medical element bins.

* * * * *